(12) United States Patent
Coleman et al.

(10) Patent No.: US 11,154,231 B2
(45) Date of Patent: Oct. 26, 2021

(54) TUNABLE, FLEXIBLE AND STRETCHABLE ADHESIVE-INTEGRATED ANTENNA

(71) Applicant: The Regents of the University of California, Oakland, CA (US)

(72) Inventors: Todd Prentice Coleman, La Jolla, CA (US); Amr Haj-Omar, La Jolla, CA (US); Yun Soung Kim, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 123 days.

(21) Appl. No.: 16/083,868

(22) PCT Filed: Mar. 13, 2017

(86) PCT No.: PCT/US2017/022204
§ 371 (c)(1),
(2) Date: Sep. 10, 2018

(87) PCT Pub. No.: WO2017/156545
PCT Pub. Date: Sep. 14, 2017

(65) Prior Publication Data
US 2019/0069788 A1 Mar. 7, 2019

Related U.S. Application Data

(60) Provisional application No. 62/307,329, filed on Mar. 11, 2016.

(51) Int. Cl.
*A61B 5/0402* (2006.01)
*A61B 5/318* (2021.01)
(Continued)

(52) U.S. Cl.
CPC ............ *A61B 5/318* (2021.01); *A61B 5/0015* (2013.01); *A61B 5/01* (2013.01); *A61B 5/24* (2021.01);
(Continued)

(58) Field of Classification Search
CPC ............................... A61B 5/0015; A61B 5/04
See application file for complete search history.

(56) References Cited

U.S. PATENT DOCUMENTS

2006/0033664 A1 2/2006 Soler Castany et al.
2007/0188327 A1 8/2007 Keetone et al.
(Continued)

OTHER PUBLICATIONS

Fan et al., "Fractal design concepts for stretchable electronics", Nature Communications, 2014, 8 pages.
(Continued)

*Primary Examiner* — Rex R Holmes
*Assistant Examiner* — Jennifer L Ghand
(74) *Attorney, Agent, or Firm* — Perkins Coie LLP

(57) ABSTRACT

Disclosed are flexible and stretchable antenna devices, systems and methods of use and manufacture. In some aspects, a flexible and stretchable antenna device includes an adhesive substrate having flexible and stretchable material properties and capable of adhering to a surface of an object; and an antenna attached on or at least partially embedded within the adhesive substrate, the antenna including a radiating element and a ground element, in which one or both of the radiating element and the ground element include a mesh structure allowing the antenna device to transmit or receive wireless communication signals at a predetermined operating frequency while being stretched.

23 Claims, 22 Drawing Sheets

(51) Int. Cl.

| | |
|---|---|
| *A61B 5/00* | (2006.01) |
| *A61B 5/01* | (2006.01) |
| *A61B 5/24* | (2021.01) |
| *A61B 5/288* | (2021.01) |
| *A61B 5/369* | (2021.01) |
| *A61B 5/389* | (2021.01) |
| *A61B 5/11* | (2006.01) |

(52) U.S. Cl.
CPC .............. *A61B 5/288* (2021.01); *A61B 5/369* (2021.01); *A61B 5/389* (2021.01); *A61B 5/6833* (2013.01); *A61B 5/11* (2013.01)

(56) References Cited

U.S. PATENT DOCUMENTS

| | | | |
|---|---|---|---|
| 2009/0262085 A1 | 10/2009 | Wassingbo et al. | |
| 2013/0041235 A1 | 2/2013 | Rogers et al. | |
| 2014/0002321 A1* | 1/2014 | Soler Castany ....... | H01Q 1/242 343/848 |
| 2015/0309326 A1 | 10/2015 | Prendergast et al. | |
| 2016/0006123 A1* | 1/2016 | Li ........................... | H01Q 7/00 343/867 |
| 2016/0218419 A1* | 7/2016 | Vance .................... | H01Q 1/241 |
| 2016/0278651 A1* | 9/2016 | Lu ........................ | A61B 5/0492 |

OTHER PUBLICATIONS

Gheethan et al., "A printed paper-based inverted F-antenna (PIFA) for WLAN applications." In Flexible Electronics & Displays Conference and Exhibition, 2009, pp. 1-5. IEEE, 2009.

Haj-Omar et al., "Adaptive Flexible Antennas for Wireless Biomedical Applications", International Microwave Symposium, 2016, 3 pages.

HFSS, Ver. 15, Ansys Inc, http://www.ansys.com/.

Hussain et al., "Metal/Polymer Based Stretchable Antenna for Constant Frequency Far-Field Communication in Wearable Electronics", Advanced Functional Materials, 2015, 25(42).

Kang et al., "Scalable Microfabrication Procedures for Adhesive-Integrated Flexible Electronic Sensors", Sensors, Sep. 2015, p. 23459-23476.

Kim et al., "Epidermal Electronics," Science 333, pp. 838-848 (2011).

Soh et al., "Wearable Wireless Health Monitoring: Current Developments, Challenges, and Future Trends", Microwave Magazine, IEEE, 16(4), 2015, pp. 55-70.

Texas Instruments app note Design note DN0007 [9] HFSS, Ver. 15, Ansys Inc, http://www.ansys.com/.

Yang et al., ""Cut-and-Paste" Manufacture of Multi parametric Epidermal Sensor Systems", Advanced Materials, 27 (41), pp. 6423-6430.

International Search Report and Written Opinion for PCT Application No. PCT/US2017/022204, dated Jul. 6, 2017, 14 pages.

* cited by examiner

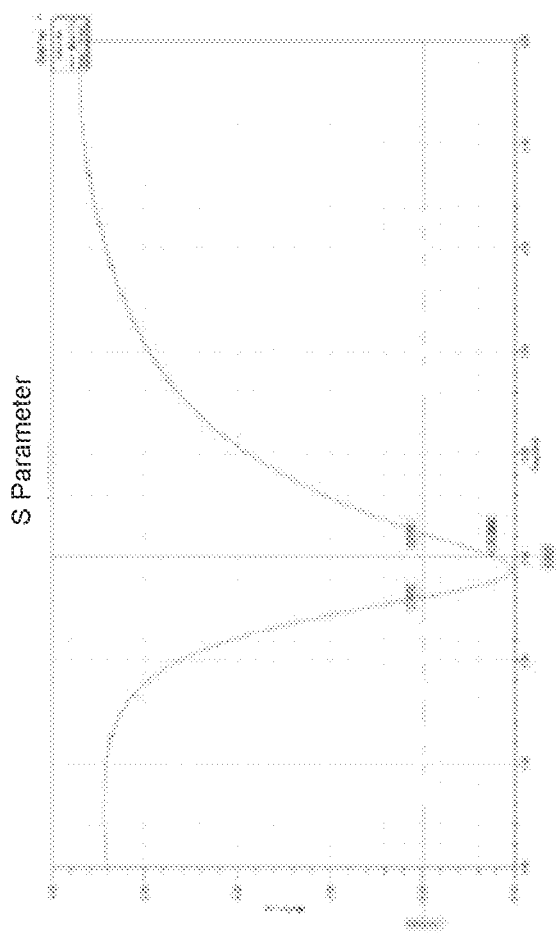
FIG. 7
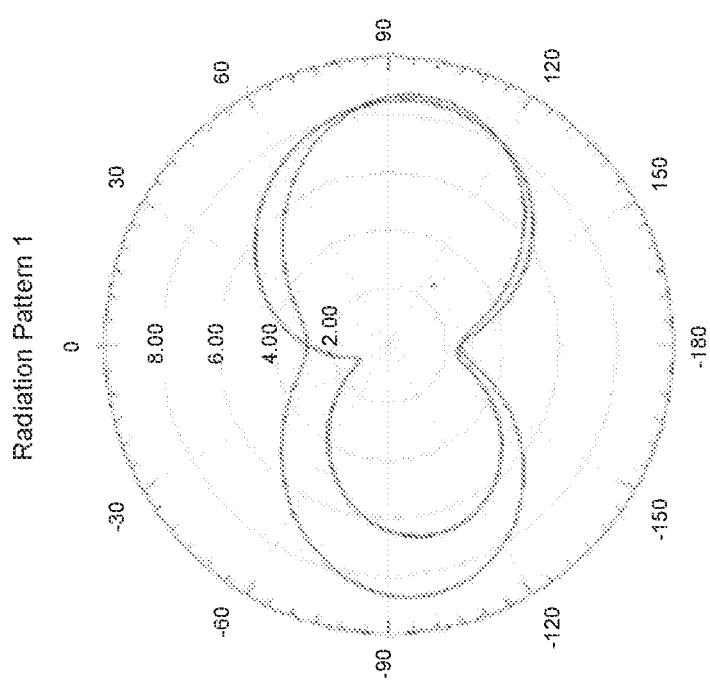

TUNABLE, FLEXIBLE AND STRETCHABLE ADHESIVE-INTEGRATED ANTENNA

This patent document is a 371 National Phase Application of PCT Application No. PCT/US2017/022204 entitled "TUNABLE, FLEXIBLE AND STRETCHABLE ADHESIVE-INTEGRATED ANTENNA" filed on Mar. 13, 2017, which claims priorities to and benefits of U.S. Provisional Patent Application No. 62/307,329 entitled "TUNABLE, FLEXIBLE AND STRETCHABLE ADHESIVE INTEGRATED ANTENNA" filed on Mar. 11, 2016. The entire contents of the aforementioned patent applications are incorporated by reference as part of the disclosure of this patent document.

TECHNICAL FIELD

This patent document relates to radio frequency antennas.

BACKGROUND

An antenna is an electrical device which converts electric signals into radio waves, and vice versa. In practice, an antenna is typically used with a radio transmitter or radio receiver. In transmission, a radio transmitter supplies an electric current oscillating at radio frequency to the antenna's electrical terminals, and the antenna radiates the energy from the current as electromagnetic waves (radio waves). In reception, an antenna intercepts some of the power of an electromagnetic wave in order to produce a voltage at the terminals, which is applied to a radio receiver to be amplified as an electrical signal.

SUMMARY

Disclosed are systems, devices and methods for stretchable, flexible, and modular antennas capable of securely attaching to nonplanar surfaces, such as the human skin, for a variety of wireless monitoring applications, including physiological monitoring.

In some aspects, a flexible and stretchable antenna device includes an adhesive substrate having flexible and stretchable material properties and structured to adhere to a surface of an object; and an antenna coupled to the adhesive substrate, the antenna including a radiating antenna part and an antenna ground part that operate to transmit or receive a wireless communication signal, in which the antenna ground part includes a mesh structure allowing the antenna to transmit or receive the wireless communication signal at a predetermined operating frequency while being stretched.

In some aspects, a device includes an adhesive substrate having flexible and stretchable material properties and structured to adhere to a surface of an object; and an antenna coupled to the adhesive substrate and including (1) a mesh of structures and openings that are interleaved to transmit or receive a wireless communication signal at a predetermined operating frequency while being stretched, and (2) an array of sensing electrodes formed in the mesh of the antenna to sense a detectable attribute of the object as a detected signal while simultaneously transmitting the detected signal in the wireless communication signal at the predetermined operating frequency.

In some aspects, a health monitoring system includes an antenna device capable of being flexed and stretched while transmitting or receiving a wireless communication signal at a particular operating frequency, the antenna device including an adhesive substrate structured to be flexible and stretchable and capable of adhering to a surface of a target including a living subject or an inanimate object associated with a medical treatment of a patient user, and an antenna coupled to the adhesive substrate, the antenna including a radiating antenna part and an antenna ground part, in which the antenna ground part includes a mesh structure including an array of features and interleaved openings, the features having a size smaller than the wavelength associated with the wireless communication signal at the predetermined operating frequency; a sensor to detect signal data associated with a detectable attribute of the target; an electronics unit including a signal conditioning unit and a transceiver unit, the signal conditioning unit to amplify and filter the detected signal data, and the transceiver unit to regulate transmission of the wireless communication signal by the antenna device; and a wireless receiver device to receive transmitted wireless communication signals from the antenna device at the predetermined operating frequency.

In some aspects, a method of fabricating a flexible and stretchable antenna includes applying a thin sheet layer of a heat and moisture resistive material to a rigid substrate that is covered with a peelable material; depositing a thin metal film over the thin sheet layer on the peelable material covered on the rigid substrate; forming an antenna structure by performing one or both of photolithography and wet etching of the thin metal film, the antenna structure formed on the thin sheet layer and structured to include a radiating antenna part and an antenna ground part, in which one or both of the radiating antenna part and the antenna ground part include a mesh structure to allow the antenna structure to undergo stretching; and producing an antenna device that is flexible and stretchable by transferring the formed antenna structure on the thin sheet layer to a flexible and stretchable adhesive material.

In some aspects, a method of producing an antenna includes providing a flexible and stretchable antenna attached on or at least partially embedded within an adhesive substrate, the antenna including a radiating antenna part and an antenna ground part, in which one or both of the radiating antenna part and the antenna ground part include a mesh structure allowing the antenna to transmit or receive a wireless communication signal at a first predetermined operating frequency while being stretched; and tuning a transmission frequency of the flexible and stretchable antenna, in which tuning includes removing a portion of at least the radiating antenna part to modify cause the antenna to transmit or receive at a second operating frequency.

In some aspects, a flexible and stretchable antenna device includes an adhesive substrate having flexible and stretchable material properties and capable of adhering to a surface of an object; and an antenna attached on or at least partially embedded within the adhesive substrate, the antenna including a radiating element and a ground element, in which one or both of the radiating element and the ground element include a mesh structure allowing the antenna device to transmit or receive wireless communication signals at a predetermined operating frequency while being stretched.

In some aspects, an electenna device includes an adhesive substrate having flexible and stretchable material properties and capable of adhering to a surface of an object; an antenna attached on or at least partially embedded within the adhesive substrate, the antenna including a radiating element and a ground element, in which one or both of the radiating element and the ground element include a mesh structure allowing the device to transmit or receive a wireless communication signal at a predetermined operating frequency while being stretched; and an array of electrodes formed in the mesh structure of the antenna configured to sense a detectable attribute of the object as a detected signal while simultaneously transmitting the detected signal in the wireless communication signal at the predetermined operating frequency.

In some aspects, a health monitoring system includes an antenna device capable of being flexed and stretched while transmitting or receiving a wireless communication signal at a particular operating frequency, the antenna device including an adhesive substrate having flexible and stretchable material properties and capable of adhering to a surface of a target including a living subject or an inanimate object associated with a medical treatment of a patient user, and an antenna attached on or at least partially embedded within the adhesive substrate, the antenna including a radiating element and a ground element, in which one or both of the radiating element and the ground element include a mesh structure; a sensor to detect signal data associated with a detectable attribute of the target, in which the sensor is coupled to the antenna device such that the antenna device is configured to transmit the detected signal data in the wireless communication signals at the predetermined operating frequency; and a software application operable on a mobile device and comprising instructions stored in a memory and processed by a processor of the mobile device, the mobile device including a wireless communications unit to receive the wireless communications signal from the antenna device.

In some aspects, a method of fabricating a flexible and stretchable antenna includes applying a thin sheet layer of a heat and moisture resistive material to a rigid substrate that is covered with a peelable material; depositing a thin metal film over the thin sheet layer on the peelable material covered on the rigid substrate; forming an antenna structure by performing one or both of photolithography and wet etching of the thin metal film, the antenna structure formed on the thin sheet layer and structured to include a radiating element and a ground element, in which one or both of the radiating element and the ground element include a mesh structure to allow the antenna structure to undergo stretching; and producing an antenna device that is flexible and stretchable by transferring the formed antenna structure on the thin sheet layer to a flexible and stretchable adhesive material.

In some aspects, a method of producing an antenna includes providing a flexible and stretchable antenna attached on or at least partially embedded within an adhesive substrate, the antenna including a radiating element and a ground element, in which one or both of the radiating element and the ground element include a mesh structure allowing the antenna to transmit or receive a wireless communication signal at a first predetermined operating frequency while being stretched; and tuning a transmission frequency of the flexible and stretchable antenna, in which tuning includes removing a portion of at least the radiating element to modify cause the antenna to transmit or receive at a second operating frequency.

In some aspects, an antenna in accordance with the present technology is stretchable, flexible, pliable, capable of permanently bonding to medical-use tegaderm through a unique fabrication process, and tunable to a user's desired operational frequency for use in a variety of biomedical and other type applications. Because of its design, the antenna can be seated on a patient's skin without the loss of the antenna's propagative qualities. Functioning of the antenna allows for the collection of the physiological data of the patient to which the device is applied. Moreover, the antenna can be also applied to nonorganic, nonconductive clinical equipment so as to facilitate data collection for patient compliance purposes, which can be in tandem with physiological monitoring of the patient. Essentially, the antenna hastens collection of patient compliance and physiological data, negating the necessity of personal employed for the collection of that data, through a miniaturized, noninvasive device.

These, and other, aspects, features, and uses are disclosed in the present document.

BRIEF DESCRIPTION OF THE DRAWINGS

FIG. 7 shows plots from an example HFSS simulation showing the $S_{11}$ parameter matched at 2.4 GHz.

DETAILED DESCRIPTION

Figure 1A:
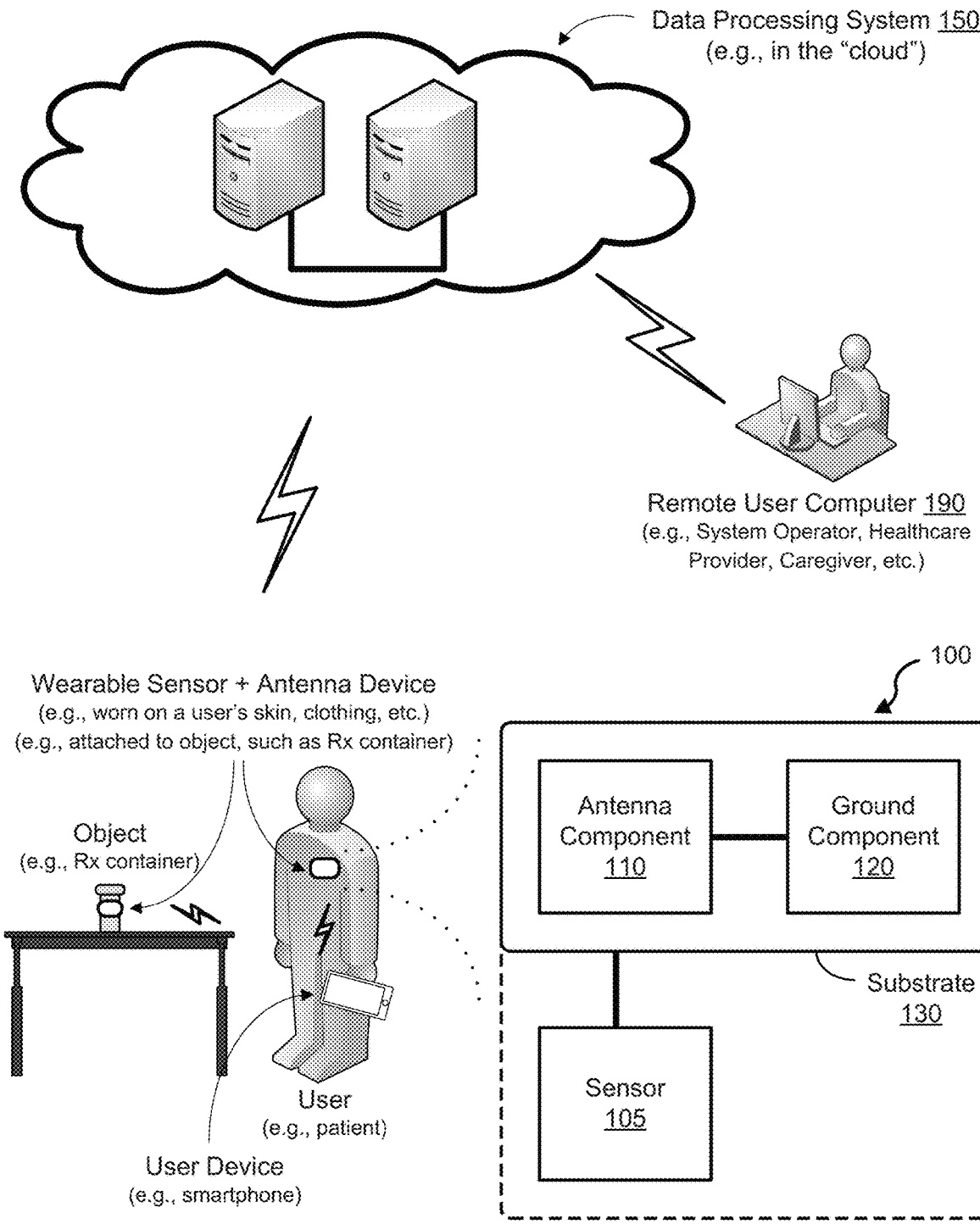
FIG. 1A shows a diagram of an example system for monitoring data obtained by a wearable sensor and flexible, stretchable antenna in accordance with the present technology.

The miniaturization of electronics and the integration of sensors and antennas into flexible, stretchable integrated materials have the potential to enable low-cost, high-fidelity physiologic monitoring in mobile settings. For example, the development of new fabrication techniques may one day allow for sensors, analog front-end (AFE) devices, and antennas to be integrated into materials about the thickness of a human hair.

Wearable sensor devices are growing in prevalence. The advancement and commercialization of wearable sensor technology currently relies on the ability to attach medical-grade physiologic sensors onto the skin using ultra-thin, flexible, and/or stretchable materials, with an increasing emphasis on creating wearable sensors using scalable, low-cost, high-yield fabrication approaches.

From the perspective of wireless operation of thin, flexible electronics, specifically for mobile health using smartphones, there are several unmet needs and challenges. For example, there has not been a practical system-level demonstration of a flexible electronic device (e.g., a wearable sensor) in terms of transmitting information from a Bluetooth transceiver via the flexible skin-integrated antenna to a smartphone. Challenges have persisted in creating antennas that are capable of bending and stretching in a manner mechanically matched to human skin so as to not interfere with the communications and performance of the antenna on such wearable devices.

Conventional antenna devices capable of portable use are typically fabricated onto printed circuit boards (PCBs) and thereby rigid in nature, making them unsuitable for certain biomedical and sensory applications, in particular untenable for attaching to human skin. Current designs of antennas that have flexible characteristics have run into problems when these antennas make direct contact with human skin. One key challenge of a viable and robust antenna capable of being worn, i.e., a 'wearable antenna', is to overcome the properties of human skin which alters the frequency propagated by the antenna. In addition, changing the shape of an antenna alters the conduct of that antenna's propagation. As such, a problem presents itself in the design of an antenna that is cheap to manufacture, flexible, pliable and easily tuned to propagate at specifically desired frequencies.

Developing electronic systems where an antenna is adhered directly to the skin poses unique problems. First, for example, the antenna must be fabricated and adhered to another material that can stretch and bend naturally with skin. Secondly, for example, the electronic system (including the antenna) must maintain consistency of function despite changes in body moisture, temperature, skin deformations and other normal bodily functions that can affect the electromagnetic properties of the antenna. These and other problems and challenges associated with conventional electronic systems and antenna devices are addressed by the present technology disclosed herein.

Disclosed are stretchable, flexible, and portable modular antenna devices capable of securely attaching to nonplanar surfaces, such as the human skin, for use in wireless monitoring, e.g., including physiological monitoring of a subject wearing a sensor device coupled to an antenna device in accordance with the present technology. The disclosed antenna devices can easily be applied to any surface, including the epidermis, and be tuned to a user desired operational frequency, e.g., such as 2.4 GHz for communication with Bluetooth-enabled devices.

Example embodiments in accordance with the present technology include designs and fabrication techniques for flexible and stretchable antennas embedded on and/or within adhesives, also referred to herein as "flex-stretch" antennas. In some aspects, a fabrication method is described for producing an inverted F antenna (IFA) that are flexible and stretchable and that can be mounted on an adhesive. Moreover, example implementations are described that demonstrate such flex-stretch antennas can be tuned and optimized, post-fabrication, for a desired frequency (e.g., 2.4 GHz for Bluetooth). As an example, an IFA design is shown for embedding within an adhesive, for which post-processing can be easily performed by a user to tune the flex-stretch antenna, e.g., simply using scissors. Such antenna designs in accordance with the disclosed technology can be optimized for different materials, e.g., including but not limited to glass, plastic, and human skin. Furthermore, example implementations are described that demonstrate a system-level use of flex-stretch antennas in transmitting digital information from a BLE transceiver to a smartphone, e.g., over 175 ft away.

Embodiments of the flex-stretch antennas in accordance with the present technology can be selectively tuned by modifying the structure of the antenna design to accommodate the type of object to which the flex-stretch antenna is to be attached, e.g., any object that an adhesive could adhere to. This provides flexibility (and stretchability) in both the physical sense and in the figurative sense, e.g., flexibility of the types of applications the flex-stretch antenna could be used. For example, antennas are designed to transmit and/or receive electromagnetic signals at a particular frequency (e.g., the operating or resonant frequency) based on what type of material and structure the antenna is to be mounted on and what type of medium the signal is to be transmitted/received. The type of material to which the antenna is mounted on has particular dielectric properties that affect (e.g., shift) the resonant frequency of the antenna's transmission. The dielectric properties differ from material to material; for example, the dielectric properties of skin are different than that of a plastic bottle. The flex-stretch antennas in accordance with the present technology include antenna designs that allow for them to operate within a flexible, pliable and stretchable adhesive and be applied to any material type (e.g., any object) based on a simple modification to the flex-stretch antenna post-fabrication. In some implementations, modification simply includes removing a predetermined portion of the antenna structure, e.g., where the predetermined portion is associated with the type of material to attach the flex-stretch antenna and/or the frequency the flex-stretch antenna is to be operated. For example, the user can cut away the appropriate portion of the antenna structure by cutting along a pre-marked line associated with the object the flex-stretch antenna is to be used. In some embodiments, for example, the flex-stretch antenna includes one or more pre-marked lines with labels associated with a material it is to be attached and operated a particular frequency, e.g., human skin at 2.4 GHz, or HDPE plastic at 2.4 GHz. As such, the flex-stretch antennas can be manufactured to a default specification associated with a particular material to attach and frequency to operate, e.g., which does not require any modifications for use, while including the pre-marked lines for cutting to allow functional application to one or more additional materials and/or operating frequencies.

The present document discloses various embodiments of an antenna that is stretchable, flexible, pliable and capable to be bonded permanently to a medical-use adhesive (e.g., tegaderm) through a unique fabrication process for ultimate biomedical applications. Because of its design, the flex-stretch antenna in accordance with embodiments of the disclosed technology can be seated on a patient's skin without the loss of the antenna's propagative qualities. In implementations, for example, the flex-stretch antenna allows for the collection of the physiological data of the patient to which the device is applied. In tandem, the flex-stretch antenna can be also applied to nonorganic, nonconductive clinical equipment so as to facilitate data collection from other sources, e.g., including in applications for patient compliance purposes. For example, the flex-stretch antenna can be used to facilitate transfer of data associated with physiological monitoring of a patient and the patient's use, e.g., compliance, of his/her medication and/or treatment regimen through a miniaturized, noninvasive device, e.g., which can negate the necessity of personnel employed for the collection of that data.

The present document discloses a fabrication method that allows for the bonding of a miniaturized, stretchable and flexible antenna permanently onto a medical-use adhesive material, such as tegaderm, for post-manufacture, biomedical applications. The fabrication process results in a wearable antenna that is thinner that a sheet of copy paper and that can be tuned post-manufacture for the user's desired propagation frequency of the antenna device. Moreover, the fabrication techniques in accordance with the present technology yield a flexible, pliable, stretchable and tunable antenna device having an end-product performance that is unaffected and unmitigated by the heat or moisture of skin. As a corollary, for example, because of device pliability, the flex-stretch antenna can also be adhered to any medicinal or clinical equipment to aid in verification of patient compliance during their use of such equipment. For example, applications of the flex-stretch antenna include wireless transfer of physiological data via wireless communication protocols, e.g., such as Bluetooth or Bluetooth Low Energy (BLE), from the device worn on patient skin or clothing to another device, such as a mobile communication device including a smartphone application, subsequently allowing transfer of data from the flex-stretch antenna device to other computing devices in the 'cloud' over the Internet.

The present document discloses an integrated electrode-antenna device, referred to herein as an "electenna", that includes an electrophysiologic electrode with a desired geometry and customized for physiological signal detection combined with a flex-stretch antenna design (e.g., IFA) in accordance with the present technology. In some embodiments of the electenna, the device includes a ground plane pattern structure designed to collect physiological signals such as electromyography (EMG), electrocardiography (ECG or EKG), electroencephalography (EEG), electrogastrography (EGG), and electrooculography (EOG) based signals while transmitting the collected signals simultaneously. Application of the electenna include, but are not limited to, assisting in collection of data pertaining to patient compliance with medical direction. For example, the electenna can be used for the accounting of patient use of prescribed medications and use of clinical equipment.

Collection of various forms of data (e.g., humidity, pressure, temperature, motion, location, etc.) through use of the miniaturized flex-stretch antenna that can easily be mounted on nonconductive surfaces with various degrees of curvature, without loss of integrity in antenna propagation. Other potential applications include, but are not limited to, mounting of a flex-stretch antenna on a variety of surfaces, e.g., such as automobile glass, consumer electronics, office equipment, etc. Essentially, the flexible and stretchable antenna facilitates wireless communications (e.g., Bluetooth, BLE, LTE, Wi-Fi, etc.) without the need for pre-purposed, rigid, built-in antenna.

FIG. 1A shows a diagram of an example system for monitoring data obtained by a wearable sensor and antenna device in accordance with the present technology. The system includes a flex-stretch antenna 100 electrically coupled to a sensor 105 wearable by a user. The system includes a data processing system 150 in communication with the flex-stretch antenna 100 electrically coupled to a sensor 105. In some embodiments, for example, the system includes a remote user computer 190 to remotely monitor data associated with the user obtained by the sensor 105 and transferred to the data processing system 150 via the flex-stretch antenna 100, and/or to remotely operate aspects of the system. For example, the remote user computer 190 can include a personal computer such as a desktop or laptop computer, a mobile computing device such as a smartphone, tablet, smartwatch, etc., or another computing device. In some implementations, for example, the system includes the flex-stretch antenna 100 electrically coupled to the sensor 105 attached to an object, e.g., such as a medicine bottle to monitor patient compliance monitoring of patient use of his/her medicine.

The flex-stretch antenna 100 includes an antenna component 110 and a ground component 120 structured on or in a flexible and stretchable adhesive substrate 130. The antenna component 110 is electrically coupled to and structurally and spatially arranged about the ground component 120 to form an antenna device. The antenna component 110 can include any one of a variety of antenna types including a monopole antenna, a dipole antenna, or other. For example, the antenna component 110 can be designed as an inverted F antenna, meandering inverted F antenna (MIFA), wire antenna, chip antenna, etc. The antenna component 110 and the ground component 120 are formed of a thin conductive layer attached to the flexible and stretchable adhesive substrate 130. The ground component 120 includes a mesh structure that provides bendability and stretchability to the structure of the flex-stretch antenna 100. The mesh structure of the flex-stretch antenna can include sub-wavelength patterns of the conductive material that forms the ground component 120 (e.g., thin metal film material) which interleave with openings to form the mesh structure. In some embodiments, the antenna component 110 can include the mesh structure, e.g., having the same or different pattern of features and openings than the mesh structure of the ground component 120. The sizing and spacing of the patterns and/or openings of the mesh structure can be configured based on the desired electrical and mechanical properties of the flex-stretch antenna 100 such that the flex-stretch antenna 100 can be stretched while propagating communication signals at the desired frequency and performance characteristics.

The substrate 130 includes a material that is mechanically flexible (e.g., bendable) and stretchable to mechanically conform to and/or match the bending and stretching ability of the material to which the flex-stretch antenna 100 is to attach. The material of the flexible, stretchable substrate 130 can include an adhesive property to enable the flex-stretch antenna 100 to securely attach to the target body, e.g., skin of the subject, surface of an object, etc. In some implementations, the substrate 130 allows for secure attachment, detachment and reattachment to the target body. For example, the substrate 130 can include, but is not limited to, a medical-use adhesive such as tegaderm, consumer grade adhesives (e.g., 3M Scotch®), consumer grade adhesives (e.g., 3M Scotch®), and other thin film materials including silicon-based, polyimide-based thin films. The substrate can be configured to have a thickness in a range of a few millimeters to tens of microns, e.g., such as 10 µm thickness. As such, for example, the flex-stretch antenna 110 can be configured to have a thickness approximate to that of a piece of copy paper (e.g., ~50-100 µm). In some implementations, for example, the sensor 105 can be formed on the substrate 130 such that the flex-stretch antenna 100 and the sensor 105 share the same flexible, stretchable substrate.

Figure 1B:
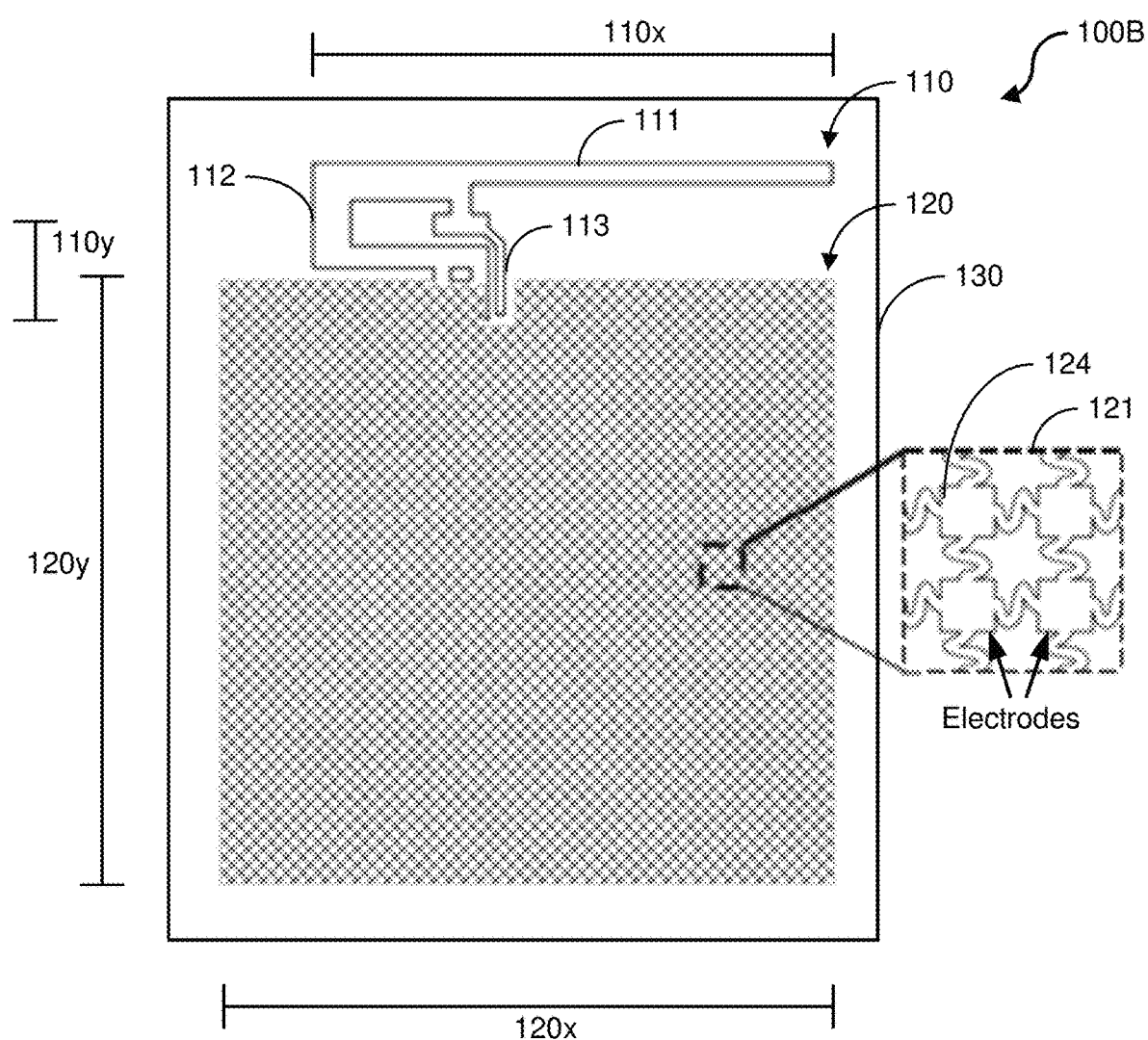
FIG. 1B shows an example embodiment of the flexible, stretchable antenna of FIG. 1A configured as an inverted F antenna (IFA).

FIG. 1B shows an example embodiment of the flex-stretch antenna 100 configured as an flex-stretch inverted F antenna 100B with a specialized design to provide robust wireless communications capability at a user-tunable operating frequency. The antenna component 110 of the example flex-stretch IFA 100B shown in FIG. 1B includes a radiating element 111, a shorting element 112, and a feed element 113 each structurally and spatially arranged with respect the ground component 120 according to the antenna design. The components of the example flex-stretch IFA 100B are configured to have a relative shape and dimensions that allow for customizable operating frequency tuning by a user. Example implementations of the example embodiment of the flex-stretch IFA 100B, described later in this document, demonstrate the efficacy of this design in transmitting data on a 2.4 GHz frequency, as well as other user-desired frequencies based on the user tuning the antenna by modifying the dimensions of the antenna design.

In the example shown in FIG. 1B, the flex-stretch IFA 100B includes a structure tuned to a 2.4 GHz communications frequency. The flex-stretch IFA 100B includes physical dimensions, where the length 120x of the ground component 120 (and overall length of the flex-stretch IFA 100B) is 35.6 mm, the width 120y of the ground component 120 is 35.6 mm, the length 110x of the antenna component 110 is 30 mm, and the width 110y of the feed element 113 of the antenna component 110 is configured to have a length to connect to an electrical terminal of the electrical circuit or electronic device to which the flex-stretch antenna 100B is to interface, e.g., maintaining a 50Ω impedance matching. In this example, the design of the example flex-stretch IFA 100B includes the end of the radiating element 111 aligning with the side-end of the ground component 120. The overall width of the example flex-stretch IFA 100B is 42.5 mm. In some embodiments, the antenna component 110 and the ground component 120 can have a thickness in the sub-micron range, e.g., such as in the tens or hundreds of nanometers.

Figure 1C:
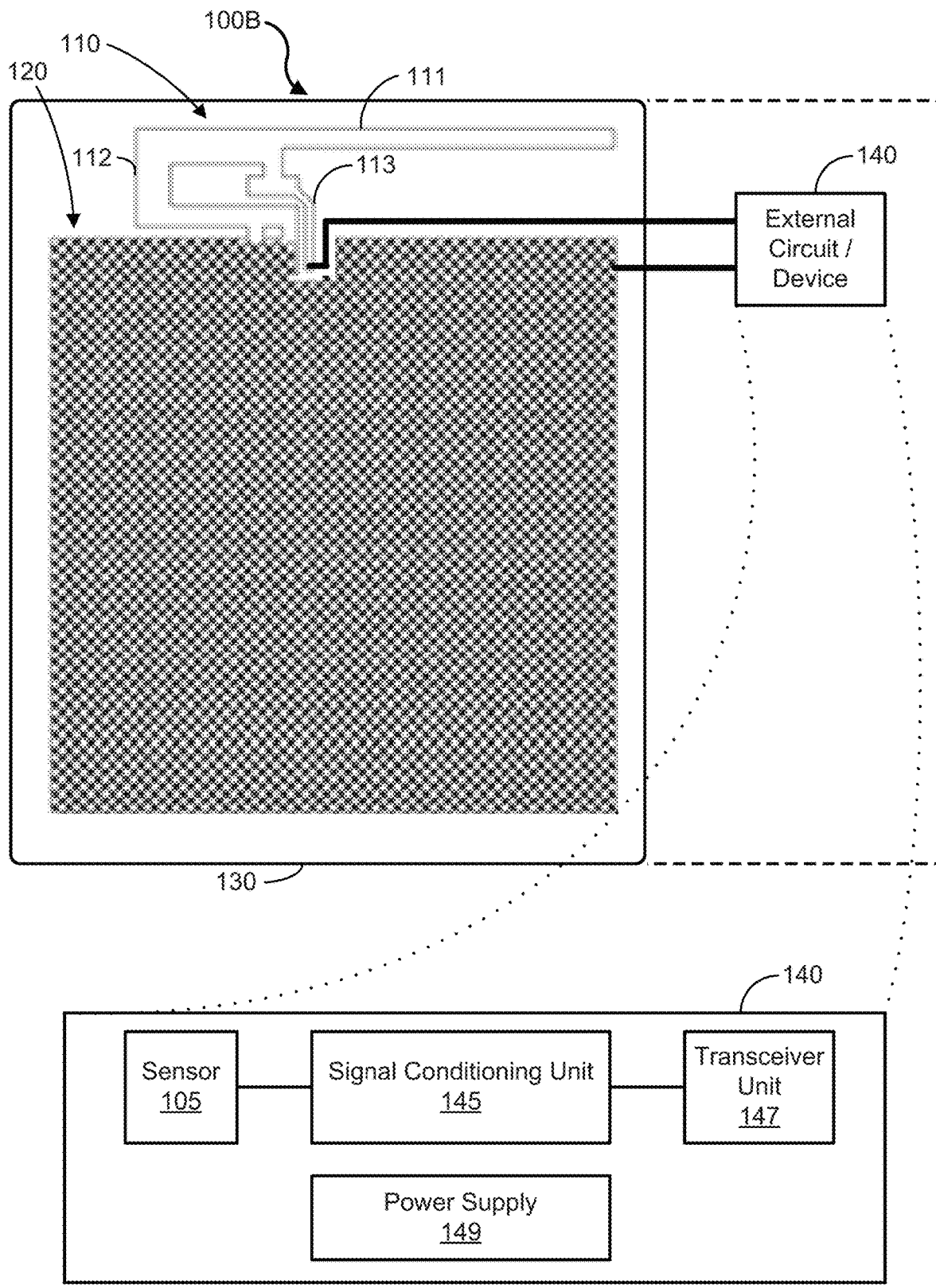
FIG. 1C shows a diagram illustrating an example implementation of flexible, stretchable antenna electrically interfaced to an external circuit.

FIG. 1C shows a diagram illustrating an example implementation of the flex-stretch IFA 100B electrically interfaced to an external circuit and/or device 140 in accordance with some embodiments of the flex-stretch IFA 100B. In this example, the external electrical circuit or electronic device 140 is connected between the feed element 113 and an element of the ground component 120, in which a signal wire of the external circuit 140 is connected to the feed element 113, and a ground wire of the external circuit 140 is connect to the ground component 120. In some embodiments, the external circuit 140 is configured on or within the flexible, stretchable substrate 130, whereas in other embodiments, the external circuit 140 is interfaced with the flex-stretch antenna 100 on a different substrate or otherwise attached to the object or nearby object. In some implementations, the external circuit 140 can include or interface with a power supply unit, e.g., such as a battery, fuel cell or other power source, to supply power to various components of the interfaced flex-stretch antenna 100 and external circuit 140 system.

The design of the example flex-stretch IFA 100B can include the feed element 113 protruding into an indentation region of the ground component 120. In some implementations, for example, the external circuit or device 140 can be configured on the flexible, stretchable substrate 130 and positioned within the footprint of the ground component 120, where the ground component 120 has a void region allowing external circuit or device components to be placed.

In some implementations, as depicted in FIG. 1C, the external circuit and/or electronics device 140 can include the sensor 105, a signal conditioning circuit or unit 145 a transceiver unit 147, and a power supply 149. The sensor 105 can capture various detectable signals of the target (e.g., living subject, inanimate object) to which it is attached, including motion signals, temperature signals, humidity signals, electrophysiological signals and electrochemical signals, among others. The signal conditioning circuit or unit 145 can include instrumentational amplifier(s) and filter(s) to condition the detected signal, e.g., improving signal-to-noise ratio. The signal conditioning unit 145 can include drive circuitry for operating the sensor 105 to perform the desired sensing mode for detecting the signals from the target. The transceiver unit 147 can include an RF front-end (RFE) that is capable of communicating with a microprocessor and manage the communication protocol of the wireless signal to be transmitted and/or received by the flex-stretch antenna 100, e.g., to add to the flexibility of the hardware, making it programmable. In some implementations, for example, the transceiver unit 147 includes a BLE chipset to communicate with a BLE-enabled device, such as a smartphone. The power supply 149 can a battery, fuel cell or other power source to supply power to the components of the external circuit and/or flex-stretch antenna 100.

Figure 1D:
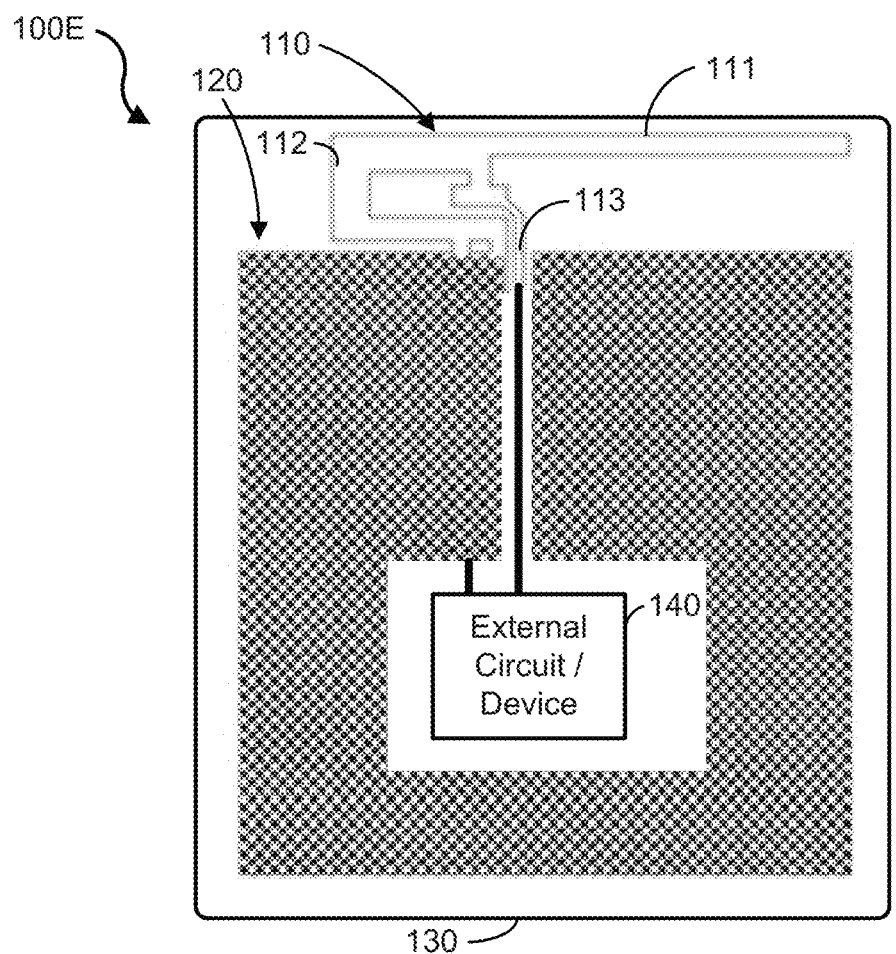
FIG. 1D shows a diagram illustrating an example implementation of a flex-stretch electenna.

FIG. 1D shows a diagram illustrating an example implementation of a flex-stretch electenna 100E. The electenna 100E includes the antenna component 110 and the ground component 120 on the flexible and stretchable adhesive substrate 130, in which the mesh structure of the ground component 120 is used as the sensor 105 for detecting electrical signals indicative of various properties of the object the electenna 100E is applied to, e.g., including electrophysiological signals, electrochemical signals, temperature measurements, humidity measurements, and pressure measurements, among others. For example, the sensors 105 formed by the mesh structure of the ground component 120 of the flex-stretch electenna 100E can be operated to measure signals at a first frequency (e.g., 1 kHz), and be operated as part of the antenna in the transmission of communication signals at a second frequency (e.g., 2.4 kHz). In the example shown in FIG. 1D, the electenna 100E includes an example embodiment of the external circuit and/or device 140 electrically interfaced to the electenna 100E, e.g., to condition the signals detected at the electrodes of the ground component 120, digitize and/or modulate the signals, and/or regulate transmission and/or reception of signals at the antenna component 110.

Referring back to FIG. 1B, the ground component 120 is structured to include an array of interconnected features 124 (shown in cut-away box 121) that forms the mesh structure of the ground component 120. In some embodiments, the mesh features 124 are configured to be 100 times smaller than the wavelength of the transmission signal to transfer (and/or receive) by the flex-stretch antenna 100. The mesh design of the ground component 120 can be optimized according to the material composition and curvature of the surface to which the flex-stretch antenna 100 would be applied. The mesh design is completely flexible, allowing conformity to any to other semi-flexible design shapes.

The interconnected features 124 of the ground component 120 in the flex-stretch IFA 100B shown in FIG. 1B includes an array of squares joined by serpentine bridges. This example structure renders the flex-stretch IFA 100B flexible, stretchable and pliable. Furthermore, for example, the square regions can allow for packing of other electrical circuit or electronic components, e.g., including but not limited to, thin-film amplifier circuits. Moreover, for example, the square regions provide a relatively large surface area suitable for detecting electrophysiological signals as electrodes in various electrophysiological applications, such as EMG, EKG, EEG, EGG and EOG. The interconnected features 124 can be designed with other geometries, e.g., such as in various electrode shape, orientation and spacing configurations, for use in electrophysiological and/or electrochemical signal acquisition applications.

Figure 1E:
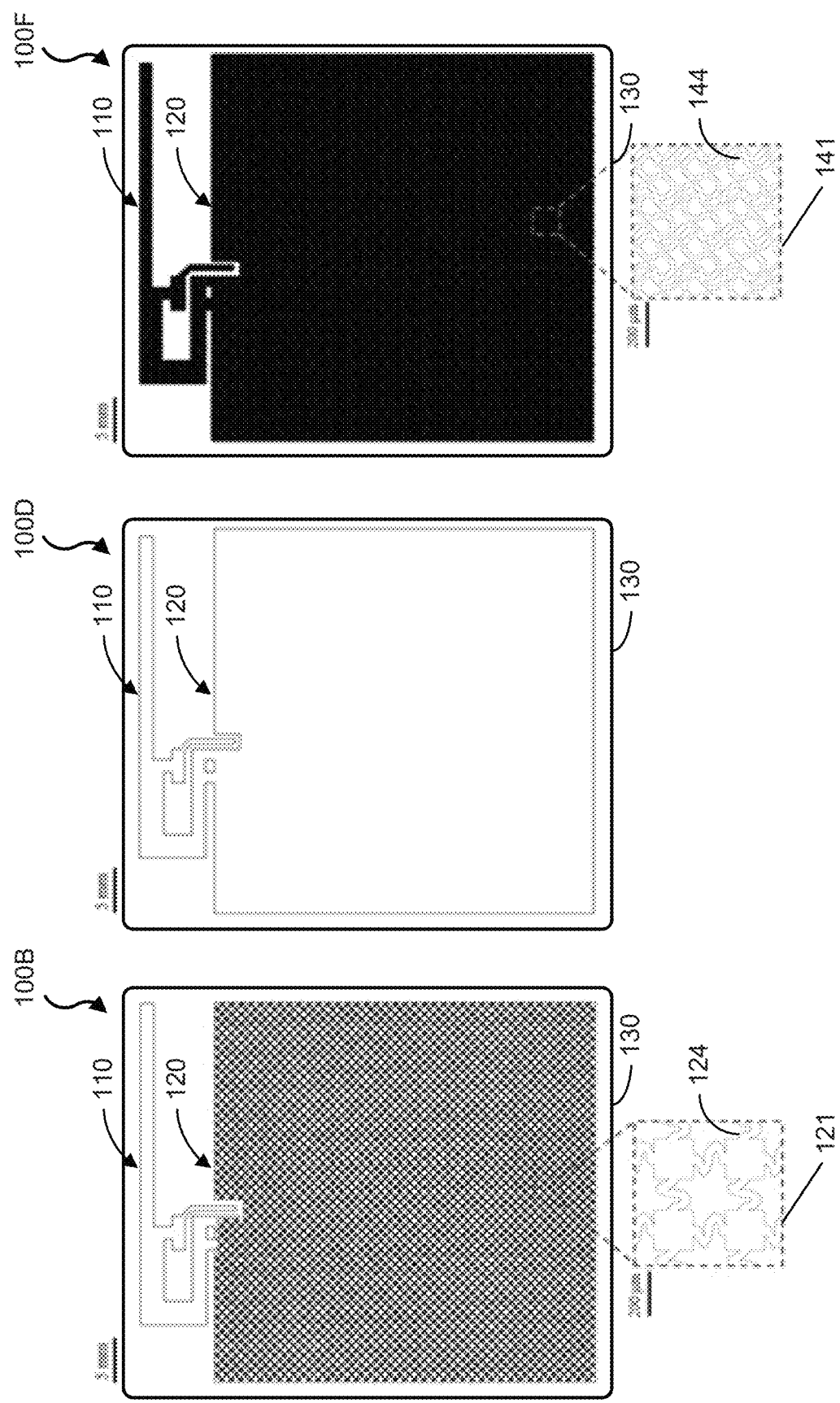
FIG. 1E shows diagrams of example embodiments of the flex-stretch IFAs.

FIG. 1E shows diagrams of example embodiments of the flex-stretch antenna 100, including the flex-stretch IFA 100B (left), a flexible IFA 100D (center), and a flexible and stretchable IFA 100F (right). The flex-stretch IFA 100F (right) includes the same or similar geometrical footprint to that of the flex-stretch IFA 100B, but differs in the design of the interconnected features 124 of its ground component 120. The flex-stretch IFA 100F includes a fully serpentine mesh pattern 144 in the ground component 120, shown in the cut-out 141. The serpentine mesh pattern 144 increases the stretchability of the antenna (e.g., relative to the flex-stretch IFA 100B). In some embodiments of the flex-stretch 100F, the antenna component 110 can also apply the serpentine mesh pattern to further maximize stretchability of the flexible, stretchable antenna.

The flexible IFA 100D (center of FIG. 1E) includes the same or similar geometrical footprint to that of the flex-stretch IFA 100B, but differs in the design of ground component 120. The flexible IFA 100D includes a solid ground component 120, allowing the antenna to be flexible, but significantly reducing the stretchability of the antenna. The various designs of the example IFAs shown in FIG. 1E provides various advantages to each of the three antenna designs with respect to the antenna's desired use case. For example, the various mesh patterns exhibited by flex-stretch IFA 100B and flex-stretch IFA 100F allow for sufficient stretchability to be mechanically matched to skin, and therefore useful for robust wearable monitoring of a subject. Flex-stretch IFA 100B and flex-stretch IFA 100F would be applicable for an example use case where the antenna is intended to both communicate and sense biopotentials of the subject. Flex-stretch IFA 100F can be advantageous in applications when an intimate contact (e.g., optimal lack of gaps) between the electrode/antenna and the skin is desired, which may increase the detection capability and render the 'cleanest' possible signals (e.g., increase signal-to-noise ratio).

Referring back to FIG. 1A, in some implementations, for example, the flex-stretch antenna 100 is in wireless communication with a mobile communication device of the user (user device), e.g., such as a smartphone, tablet or other wearable computing or communication device like a smartwatch, smartglasses, etc. In such implementations, the flex-stretch antenna 100 transfers data from the sensor 105 to the user device, which can in turn transfer data to the data processing system 150.

In some implementations, for example, the sensor 105 can include a electrophysiological sensor such as an EEG, EKG, EMG, EGG, EOG sensor, an electrochemical sensor, and/or other type of sensor, for monitoring physiological data of the user (e.g., patient user). For example, the sensor 105 can include a temperature sensor, a humidity sensor, a pressure sensor, a motion sensor, or a location sensor. Similarly, the device electrically coupled to the flex-stretch antenna 100 can include, additionally or optionally, an actuator device, e.g., such as a medicinal delivery device, alert or alarm device, and/or other type of actuator device.

In some embodiments, the data processing system 150 includes one or more computing devices in a computer system or communication network accessible via the Internet (referred to as "the cloud"), e.g., including servers and/or databases in the cloud. In some embodiments, the data processing system 150 can be embodied on the user device (e.g., smartphone). In such embodiments, for example, the data processing system 150 can include a software application ("app") that is stored on the user device and controls the processing and storage of the data received via the flex-antenna 100 using the processor and memory of the user device. Similarly, in some embodiments of the system, for example, the data processing system 150 includes the one or more computing devices in the cloud and the app resident on the user device to receive and manage data processing of the data obtained by the sensor 105. In some implementations, for example, the flex-stretch antenna 100 transfers data to the user device, e.g., using a low power wireless communication protocol (e.g., BLE), which the app can control various data processing of the received data; and the app can transfer the data to the one or more computing devices in the cloud using a different communication protocol, e.g., including a wired or a wireless communication protocol such as LTE, Wi-Fi, or other.

Figure 1F:
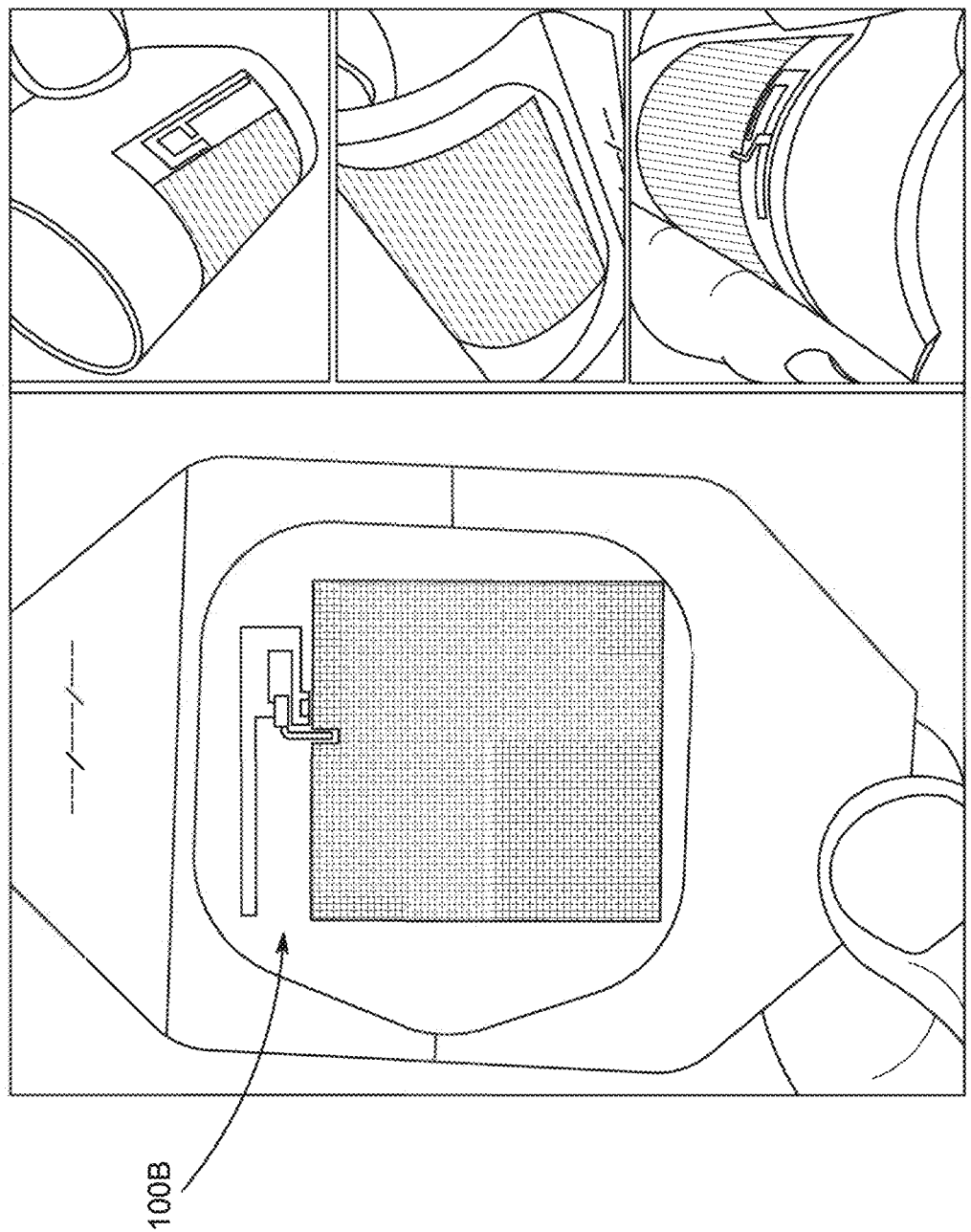
FIG. 1F shows images of an example antenna embodiment in which the peelable, flexible nature of the antenna is depicted.

FIG. 1F shows images of an example antenna embodiment in which the peelable, flexible nature of the antenna is depicted. The images of FIG. 1F depict an example of the flex-stretch IFA 100B that is packaged and ready for quick peel-off and placement on a subject's body (e.g., skin). The images also depict the example flex-stretch IFA undergoing various degrees of bending and folding.

Modification to the overall shape of the flex-stretch IFA or relative layout or orientations of the elements of the antenna component 110 can affect a shift in resonant frequency. The design of the example flex-stretch IFA allows for simple modification by a user post-fabrication to configure the flex-stretch IFA to transmit or receive at user-desired frequency and on a user-desired object. For example, while other antenna types may be smaller and would reduce footprint of the flex-stretch antenna, the example flex-stretch IFA has a size that better facilitates the user accurately tuning the antenna by him/herself without expensive or cumbersome processes (e.g., user can simply tune the antenna by cutting a region with scissors). Moreover, the design of the example flex-stretch IFA accounts for robust use in applications where the antenna structure is going to be stretched and/or flexed continuously and indefinitely, including in multiple dimensions, e.g., vertically, horizontally or diagonally. Changes in the structure of an antenna can distort the signal and shift the resonant frequency. Conventional antenna designs, including conventional IFAs, do not account for such use cases involving significant stretching and flexing. The example flex-stretch IFA includes a design capable of withstanding vigorous stretching and flexing while successfully transmitting and/or receiving signals.

Figure 1G:
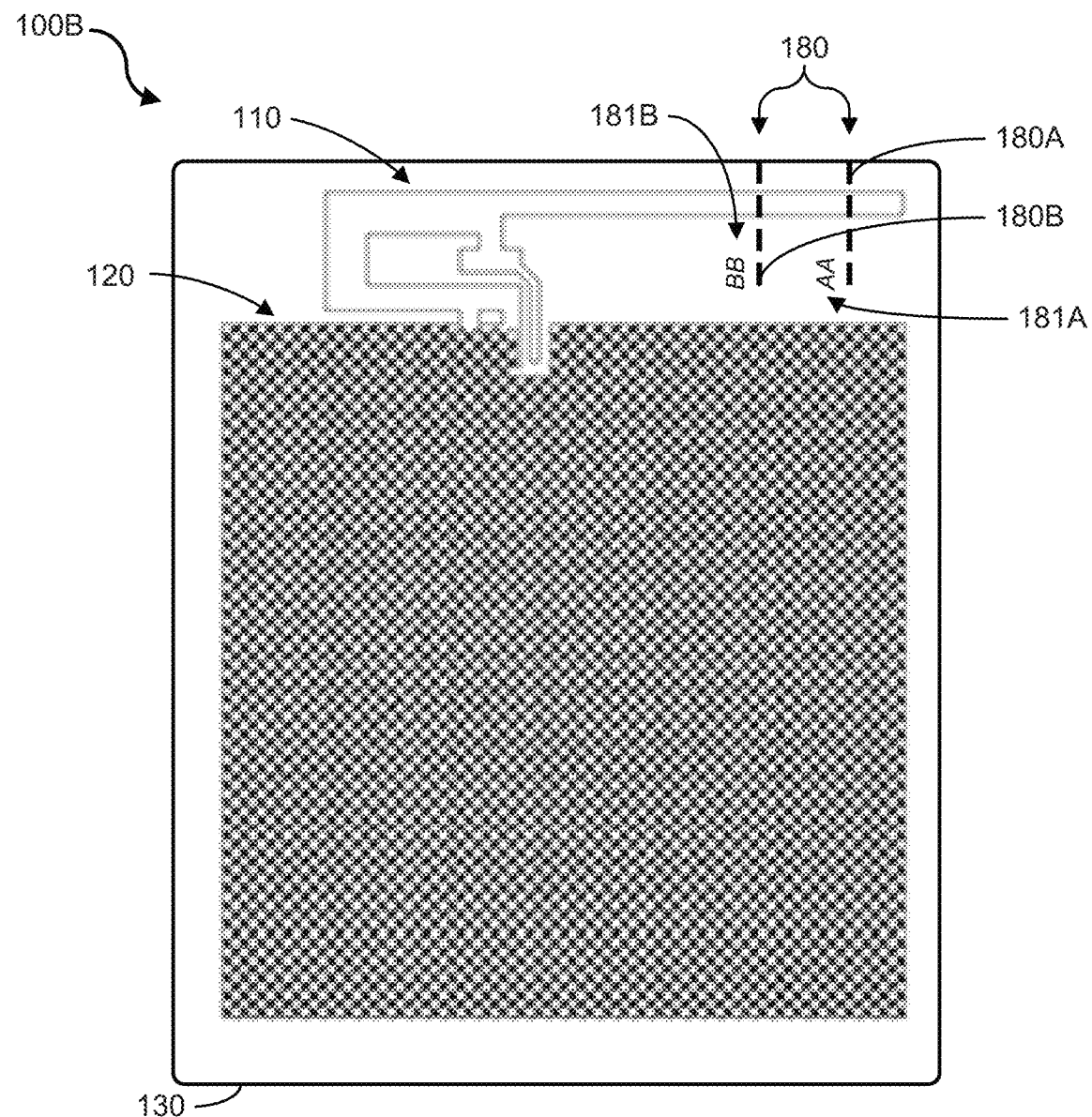
FIG. 1G shows an example of the flex-stretch antenna including pre-marked lines on for tuning the antenna by a user.

FIG. 1G shows an example of the flex-stretch antenna 100B including pre-marked lines 180 on the substrate 130 for tuning the antenna by a user cutting along a pre-marked line to remove a predetermined portion of the antenna structure. As shown in the diagram of FIG. 1G, a pre-marked line 180A is provided on the substrate 130 that is associated with a particular resonant frequency for a particular material, which optionally may be accompanied include a label 181A proximate the pre-marked line 180A. Similarly, a pre-marked line 180B is provided on the substrate 130, which optionally may be accompanied by a label 181B proximate the pre-marked line 180B, in which the pre-marked line 180B is associated with the particular resonant frequency for another type material the flex-stretch antenna 100B is to be applied, and/or is associated with another resonant frequency for the target material as pre-marked line 180A or another material type. The labels can include names or symbolic representation of the material type and/or operating frequency for recognition by the user. It is understood that the flex-stretch antenna 100B can include none, one or multiple pre-marked lines 180.

Figure 1H:
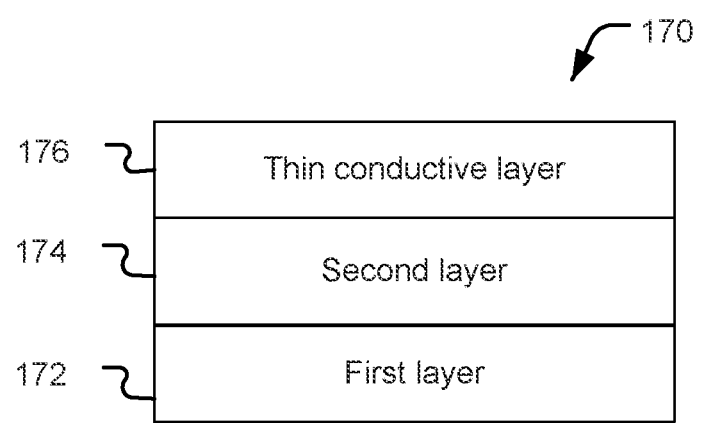
FIG. 1H illustrates a cross section of an example embodiment of a flexible, stretchable antenna showing layers of an inverted-F antenna.

FIG. 1H illustrates a cross section showing the material layers of an example embodiment of a flex-stretch antenna 170 in accordance with the present technology. The antenna 170 includes the substrate 130 including a first layer 172 made up of a flexible, stretchable and adhesive material, e.g., such as tegaderm, and a second layer 174 over the first layer made up of an insulating layer that allows a conductive material to adhere, e.g., such as a polyimide. In some implementations, the second layer 174 includes a material with heat and moisture resistant properties. The antenna component 110 and the ground component 120 are made of a conductive layer 176 (e.g., a thin metal film layer) over the second insulating layer 174, e.g., in which the thin metal film layer 176 is shaped to resemble the antenna design such as an inverted F shape in accordance with the flex-stretch antenna designs of the present technology. In implementations, for example, the second layer 174 may be present between the first layer 172 and the metal layer 176, and not exposed on other regions of the substrate 130. In some implementations where the first layer 172 is a material possessing surface properties that can adhere the thin conductive layer 176, for example, the substrate 130 includes the first layer 172 (e.g., tegaderm) and the conductive layer 176 (e.g., thin metal film layer) formed on the first layer 172.

Figure 2A:
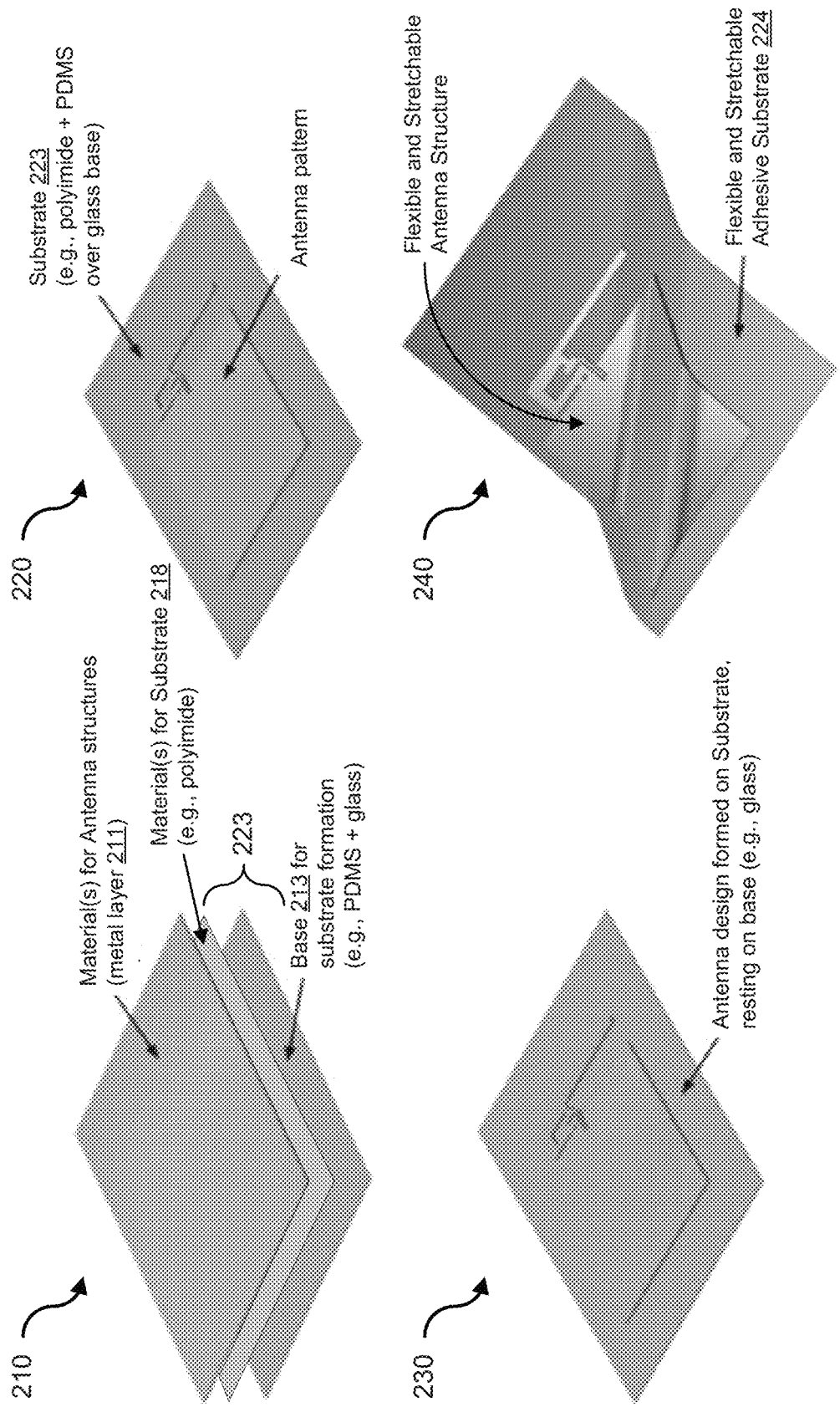
FIG. 2A shows an illustrative diagram of an example fabrication technique to produce a flex-stretch antenna in accordance with the present technology.

FIG. 2A shows an illustrative diagram of an example fabrication technique to produce a flex-stretch antenna in accordance with the present technology. The fabrication method includes a process 210 to form a base substrate 213 for formation of the flexible and stretchable substrate, in which a substrate material layer 218 and a conductive material layer 211 for the antenna is deposited over the base substrate 213. In some implementations, the process 210 includes laminating a thin sheet of a polyimide (e.g., Kapton film, 12.5 µm) onto a glass slide coated with polydimethylsiloxane (PDMS) to create the formation substrate 223; and the process 210 includes depositing (e.g., via sputter deposition) one or more thin metal films to form the antenna layer 211 (e.g., Cr/Au, 10 nm/200 nm). The fabrication method includes a process 220 to form the antenna structure on the formation substrate 223. In some implementations, the process 220 includes forming the antenna structures by photolithography and wet etching to define the shape features of the antenna pattern. In some implementations, for example, the exposed regions of the Kapton sheet can be optionally removed through oxygen reactive ion etching process utilizing the metal patterns as the dry etch mask. At this point, the antenna layer is completed and can be directly peeled-off of the PDMS surface of the base (process 230) and transferred to an adhesive material of choice, for example, Tegaderm (3M, USA). The fabrication method includes a process 230 to remove (e.g., peel-off) the formed antenna structure from the base substrate 213 (e.g., PDMS and glass). The fabrication method includes a process 240 to transfer the formed antenna structure on an adhesive material substrate 224 (e.g., Tegaderm). In some implementations, for example, the flexible and stretchable adhesive substrate 224 is laminated onto the antenna structure over the formation substrate 223 to attach to the exposed antenna structure and peel the antenna structure from the formation substrate 223, retaining the antenna structure on the flexible and stretchable adhesive substrate 224. In some implementations, for example, the processes 230 and 240 includes peeling off the antenna structure and attaching to the adhesive material (of the flexible and stretchable substrate 224) by using an intermediary water soluble tape, in which the water soluble tape would be subsequently dissolved and the antenna structure would be attached to the flexible and stretchable substrate 224.

Traditionally, flexible electronics based on thin-film microfabrication techniques involved the dissolution of a sacrificial layer in order to "lift-off" the electronics from the donor substrate. Such conventional flexible electronics fabrication methods typically require submerging the completed electronics into a solvent bath (e.g., acetone). Because the nature of the dissolution of the sacrificial layer is not controllable, the released electronics may not retain its intended shapes and features. Moreover, the placement of the metal structures is limited only to the top most layer. Due to this limitation, one must conduct a 'double-transfer' of the electronics if the final desired configuration, for example, is an adhesive-integrated with the electrode facing the skin. Such conventional methods require not only more time and resources, but also more error-prone due to the "lift-off" step.

The example fabrication process shown in FIG. 2A bypasses the "lift-off" step as well as obviates the need for one of the two transfer steps. This is done by building the electronic structure upside down on a PDMS-coated substrate, for example, which is just sticky enough to hold the film structures during the microfabrication steps, but weak enough to release them to target adhesives. Because the device is constructed upside down, the metal layer (e.g., metal antenna structure) is already facing downward. Thus, the target adhesives can be directly applied to peel off the device in a way that the same desired configuration is achieved.

In some implementations of the fabrication method shown in FIG. 2A, a flex-stretch antenna device can use the PDMS-coated substrates for manufacture of the flex-stretch antenna devices and any other flexible and stretchable electronics device. As an example, the flexible and stretchable electronic device to be fabricated could be done on a PDMS-coated wafer, e.g., either "inverted" or "non-inverted". There is still the benefit of the single step integration into the target adhesives, but depending on the use case, one can decide the placement of certain metal layers. If one doesn't need the metal layer to make a direct contact with skin (e.g., a flex-stretch antenna for a non-electrophysiological application, such as mounting on a bottle for monitoring its use), then one can use another fabrication method in accordance with the present technology, shown in FIG. 2B.

Figure 2B:
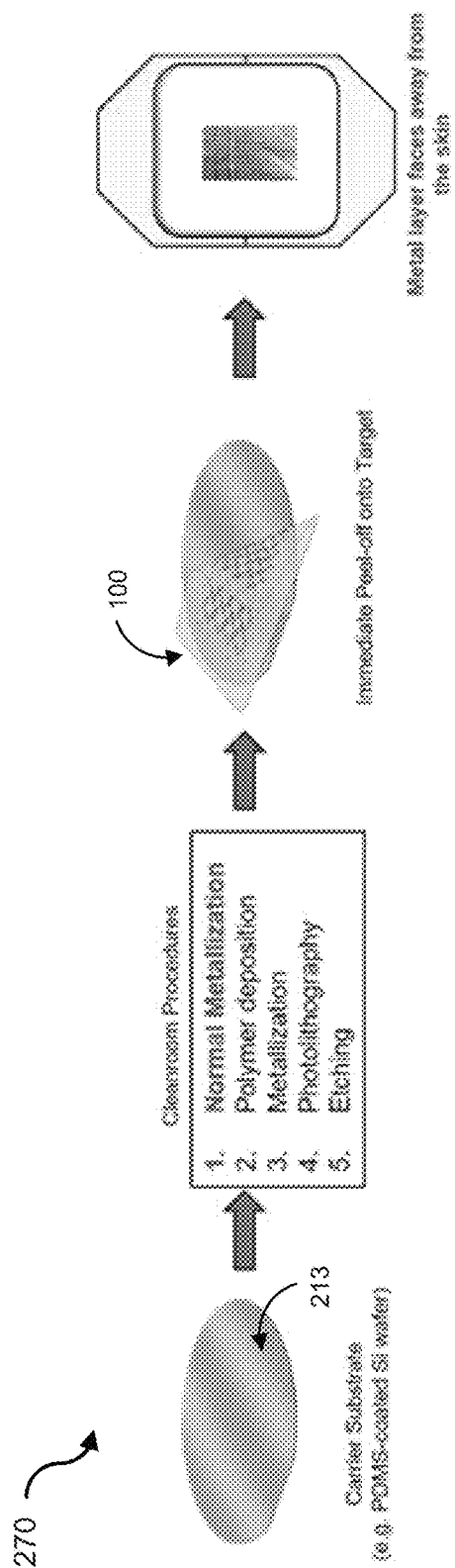
FIG. 2B shows an illustrative diagram of a fabrication method to produce an adhesive-integrated stretchable antenna in accordance with the present technology.

FIG. 2B shows an illustrative diagram of a fabrication method 270 to produce an adhesive-integrated stretchable antenna where the metal layer is located either within the polymer layers, or in contact with the adhesive. As shown in diagram, a flex-stretch antenna can be fabricated upside down on the base substrate 213 (e.g., PDMS and glass). The method 270 includes depositing the metal layers 211 first, then depositing the intermediary substrate material 218 (e.g., polyimide) second. As such, for example, the metal layer 211 to form the antenna structure can face the skin directly away from the flexible and adhesive substrate 224. The method 270 can be implemented for applications where the flex-stretch antenna 100 is to be used in a system to function as an "electenna" device, for example, as direct contact between the metal "electrode" represented by the mesh structure of the flex-stretch antenna 100 and skin is desired. For example, this example microfabrication method 270 obviates the need for a double-transfer process, and allows a single, direct integration of the antenna into the adhesive substrate (e.g., tegaderm).

In this sense, the present technology includes two ways to produce adhesive-integrated flexible and stretchable electronic devices, such as flex-stretch antennas. If the application of the produced flexible and stretchable electronic device requires the structures formed by the metal layer to be in contact with skin (e.g., such as an electenna device), then the preferred fabrication method is that shown in FIG. 2A and FIG. 2C. If the application of the produced flexible and stretchable electronic device does not require the structures formed by the metal layer to be in contact with skin, then the fabrication methods described in any of FIGS. 2A, 2B and 2C can be used.

Figure 2C:
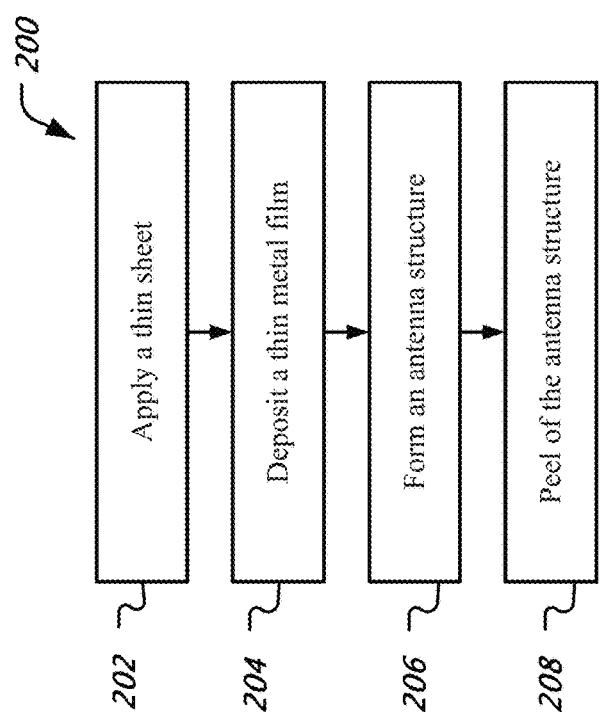
FIG. 2C shows a flowchart of an example method of fabricating flexible, stretchable antennas in accordance with the present technology.

FIG. 2C shows a flowchart for an example embodiment of a method 200 for antenna fabrication. At 202, the method 200 includes applying a thin sheet of a heat and moisture resistive material to a rigid substrate that is covered with a peelable material. In some embodiments, the heat and moisture resistive material may be a polyamide film material such as Kapton. At 204, the method 200 includes depositing a thin metal film over the thin sheet and the rigid substrate. The thin metal film may be made of chromium and/or gold, and may have a thickness between 10 to 200 nm. At 206, the method 200 includes forming an antenna structure, e.g., which can include performing photolithography and wet etching of the thin metal film. The wet etching process may thus expose the antenna structure having a desired shape, such as an IFA antenna. At 208, the method 200 includes peeling off the antenna structure from the rigid substrate. In some implementations, at 208, the method 200 includes transferring the peeled-off antenna structure to an adhesive substrate, forming a flexible, stretchable and adhesive antenna, such as the various embodiments of the flex-stretch antenna 100 descried herein. In some embodiments, the method 200 may further include tuning the antenna to meet a target radio frequency (RF) performance. In some implementations, the tuning the antenna includes removing a portion of the antenna structure corresponding to a particular resonant frequency at which the remaining antenna structure would operate.

Figure 2D:
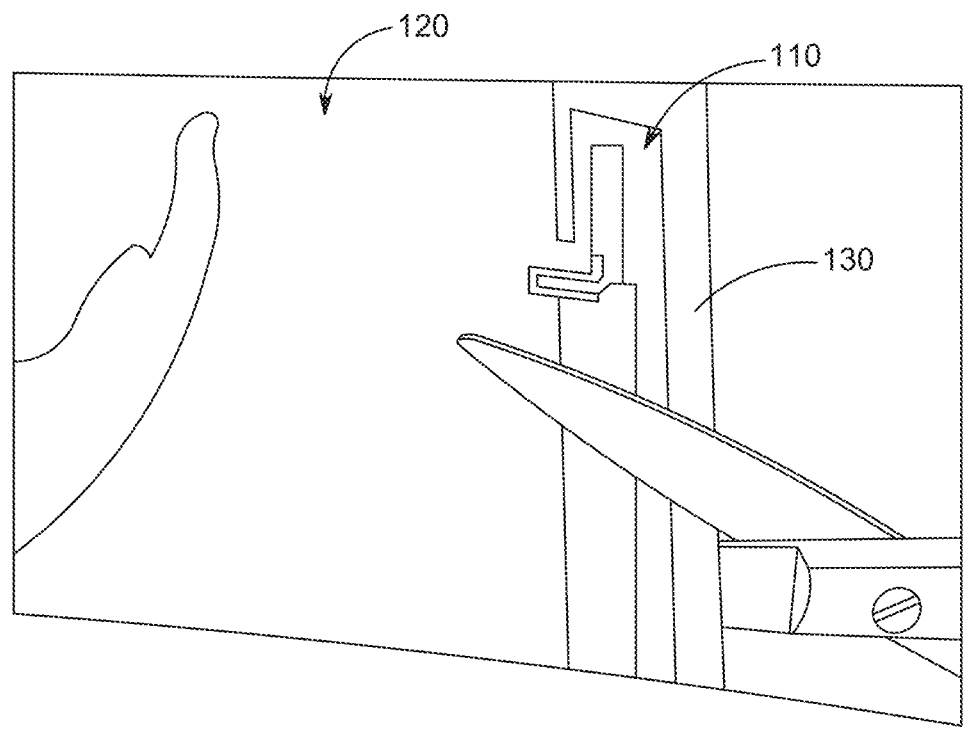
FIG. 2D shows an image of a user tuning an example flexible and stretchable antenna by cutting with scissors.

FIG. 2D shows an image of a user tuning an example flex-stretch antenna by removing a portion of the antenna structure through cutting with scissors.

Figure 3:
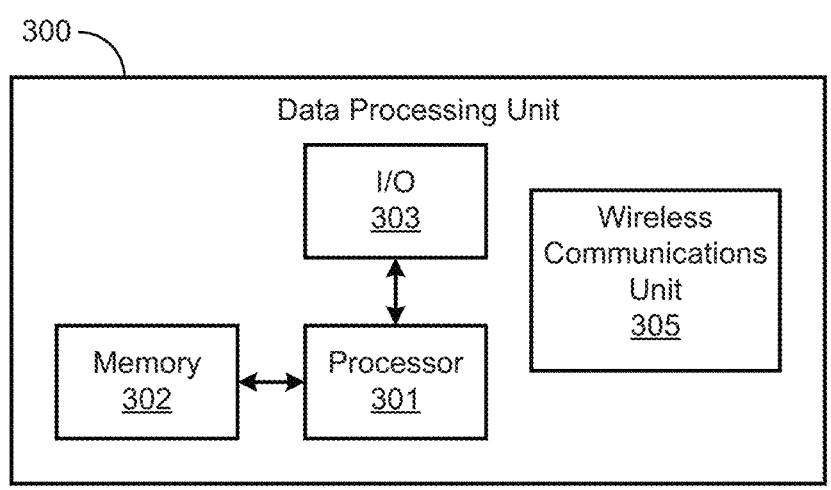
FIG. 3 shows a block diagram of an example embodiment of a data processing unit of the data processing system.

FIG. 3 shows a block diagram of an example embodiment of a data processing unit 300 of the data processing system 150 to process the data obtained by the sensor 105 and provided to the data processing system 150 by the flex-stretch antenna 100. In some implementations, the data processing unit 300 is embodied on the one or more computing devices in the cloud and/or the app resident on the user device. The data processing unit 300 can include a processor 301 to process data, and a memory 302 in communication with the processor 301 to store and/or buffer data. For example, the processor 301 can include a central processing unit (CPU) or a microcontroller unit (MCU). For example, the memory 302 can include and store processor-executable code, which when executed by the processor, configures the data processing unit 300 to perform various operations, e.g., such as receiving information, commands, and/or data, processing information and data, and transmitting or providing information/data to another device. To support various functions of the data processing unit 300, the memory 302 can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory 302. In some implementations, the data processing unit 300 includes an input/output unit (I/O) 303 to interface the processor 301 and/or memory 302 to other modules, units or devices associated with the data processing system 150, and/or external devices. The data processing unit 300 includes a wireless communications unit 305, e.g., such as a transmitter (Tx) or a transmitter/receiver (Tx/Rx) unit. The I/O 303 can interface the processor 301 and memory 302 with the wireless communications unit 305 to utilize various types of wireless interfaces compatible with typical data communication standards, for example, which can be used in communications of the data processing unit 300 with other devices such as the flex-stretch antenna 100 or a similar data processing unit 300 on another device, e.g., such as between the one or more computers in the cloud and the user device. The data communication standards include, but are not limited to, Bluetooth, Bluetooth low energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. In some implementations, the data processing unit 300 can interface with other devices using a wired connection via the I/O of the data processing unit 300. The data processing unit 300 can also interface with other external interfaces, sources of data storage, and/or visual or audio display devices, etc. to retrieve and transfer data and information that can be processed by the processor 301, stored in the memory 302, or exhibited on an output unit of the user device (e.g., smartphone) or an external device.

Example Implementations

Described below are implementations of example embodiments of the systems, methods and devices in accordance with the present technology to wirelessly monitor physiological data of subjects using a stretchable, flexible, and wearable antenna device mounted to nonplanar surfaces including the subjects' skin. A study, for example, was conducted using an example embodiment of the flexible and stretchable antenna embedded within an FDA-approved medical grade adhesive. The antenna was mounted on a subject's biceps as the subject performed a stress test, demonstrating the desired antenna function as it was stretched, flexed and exposed to sweat. The antenna was tested at a functioning system level and was able to communicate via BLE up to 175 ft to the subject's smartphone device employing a customized iOS smartphone application ("app"). The results of the example study demonstrated that the example IFA device was capable of effectively and reliably transmitting the acquired physiological data from the subject to another device, e.g., for subsequent processing and/or other purposes. Moreover, the example results of the antenna used in the experiment were compared to simulations and system-level test results.

Figure 4:
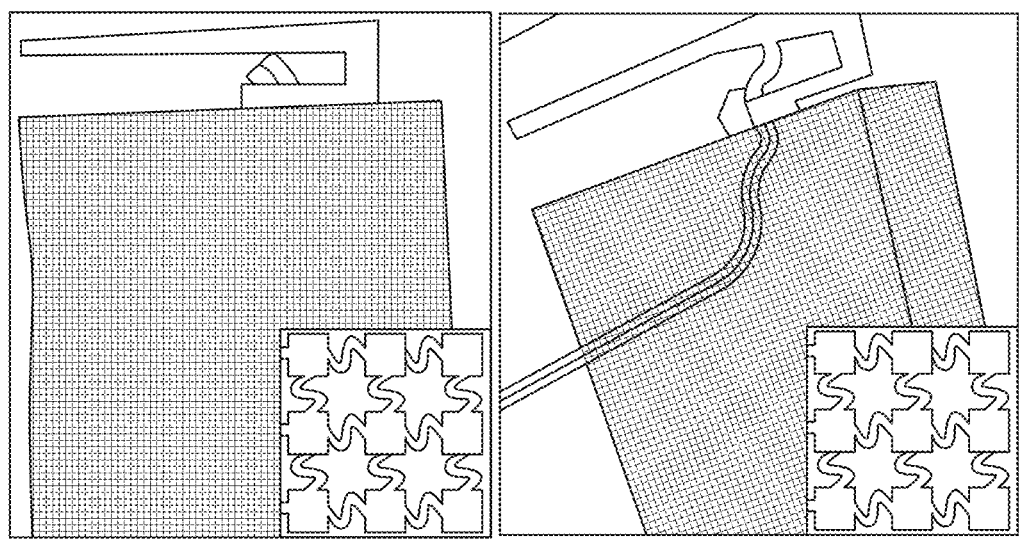
FIG. 4 shows photos illustrating the stretching of an example antenna device and the mesh pattern.

The study first included a calibration test using an off-the-shelf PCB antenna to establish a control for a reliable and repeatable communication means to a smartphone. An example flexible, stretchable IFA device in accordance with present technology was fabricated where the IFA was built on a flexible substrate and embedded in Tegaderm. The example IFA device used in the study included a "meshed" metallization structure to achieve flexibility while maintaining electrical RF performance. While the appearance of a meshed metal surface may resemble a fractal type antenna, for example, the meshing feature of fabricating the example IFA includes removing metal in sub-wavelength patterns that do not significantly perturb the surface currents on the antenna, thereby allowing the antenna to radiate as if it was a solid layer of metal. In addition, applying a mesh to the antenna can increase its stretchability, e.g., including up to 30%, making it more similar to human skin, as illustrated in FIG. 4. FIG. 4 shows photos illustrating the stretching of the example IFA device and the resultant variation of the mesh pattern during stretching. The left image of FIG. 4 shows the IFA at 0% stretch, and the right image of FIG. 4 shows the IFA undergoing 30% stretch.

Figure 5:
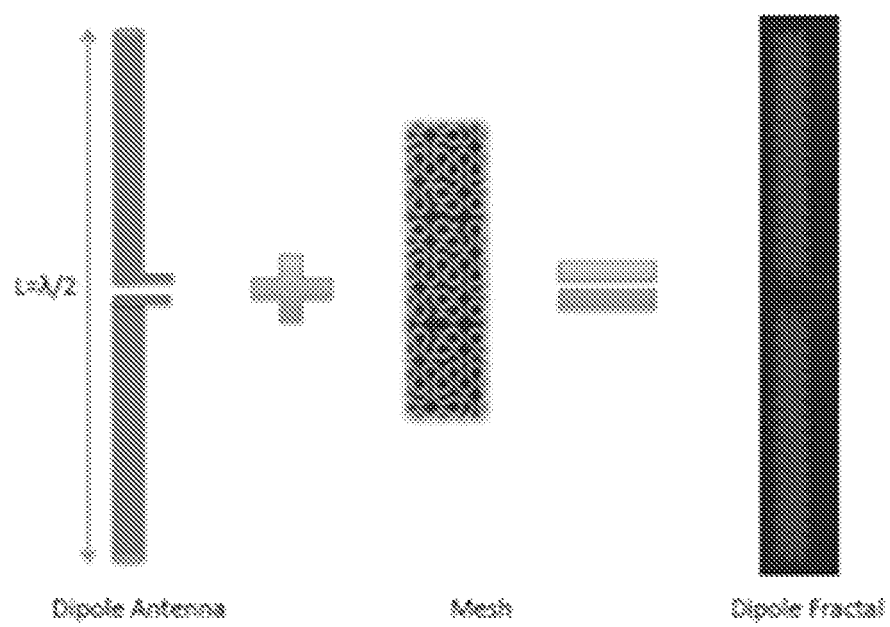
FIG. 5 shows diagrams depicting a mesh applied on a dipole antenna and simulation results of the dipole antenna producing an omnidirectional radiation pattern.
Figure 5:
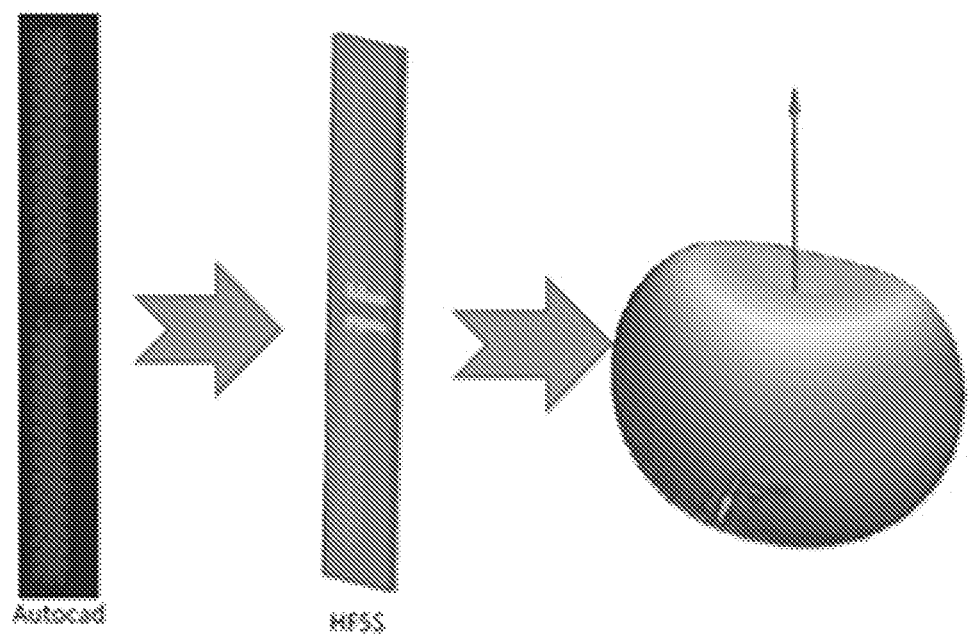

Validation of the meshed antenna concept was performed using simulations. For example, a mesh simulation of a dipole antenna was determined to have a radiation pattern similar to an omnidirectional antenna propagating equally in all directions with a null in the z-axis. FIG. 5 shows a diagram depicting a mesh applied on a dipole antenna (top) and a diagram depicting simulation results of the dipole antenna producing an omnidirectional radiation pattern (bottom). Furthermore, an RF bench setup test was constructed by connecting the mesh dipole (device under test (DUT)) to a spectrum analyzer to receive a signal from a 2.4 GHz Signal Generator transmitting via a TI IFA PCB antenna. The mesh dipole was placed in various orientations while varying the displacement of the antenna up to 1 meter apart. The example results were invariably higher than −50 dBm, which is higher than the −89 dBm, e.g., the sensitivity level of the BLE transceiver.

Various antenna types were compared for use at 2.4 GHz, e.g., for BLE applications, with meshed antenna designs in accordance with the present technology. For example, the study included a meandered inverted F antenna (MIFA), an IFA, a chip antenna, and a wire antenna. For health monitoring applications, key considerations for antenna design include low cost, reliability and minimal size. An IFA was selected for example implementations in the study for its high ranking among all of these consideration criteria, e.g., as compared to the MIFA, chip antenna and wire antenna. It is noted that existing designs of a chip antenna would occupy the smallest area, but is not currently as cost effective as the IFA.

The purpose of an antenna is to translate electrical signals into electromagnetic waves in free space that enable wireless communication. An antenna creates oscillating currents and associated charges that include a propagating electromagnetic field. In conventional miniaturized PCB applications, there is limited power. In order to optimize the power radiated, the board impedance must match 50-ohms, for example, which is the convention in RF communication. The better the match, the lower the reflection, and hence the higher the efficiency of the antenna, e.g., allowing for longer range of operation as well as better sensitivity at the receiver side, and allowing it in turn to pick weak signals. An antenna is a conducting material with a feed that allows the accelerated current charges to radiate off a sharp edge.

The IFA antenna can be thought of as half a slot antenna. A slot antenna length is equal to half the wavelength. The ground plane height is at least half the length of the antenna and as wide as the length of the antenna. The voltages at both ends of the slots are zero since they are shorted and maximum at quarter wavelength, which is the center of the slot. When applying transmission theory the center point is similar to having an open circuit, removing half the slot antenna converts it into an IFA antenna.

Return loss ($S_{11}$) is the ratio of the incident power to reflected power in dB. It is a measure that indicates how well the antenna is matched to 50-ohms impedance. In general practice, for example, if the matching is within 5 percent tolerance, the matching network can be optimized to correct for any capacitance and reactance. The system is tuned by altering the value of the capacitor or inductor so that the smith chart is matched to the center point where load is 50 ohms. A 3 dB return loss means that half of the power is lost and the other half is reflected. A return loss greater than 10 dB implies more than 90 percent of the power is radiated outwards. The $S_{11}$ was −12 dB for the example simulations and measurements using the example IFA.

For the purposes of these example implementations, bandwidth is defined as 90 percent transmission power points from the cutoff frequency. This indicates the reliable frequency ranges of operation, which is dependent on how well the antenna's impedance matches to 50-ohms. The example antenna in the study had a bandwidth of around 300 MHz.

Figures 6A, 6B:
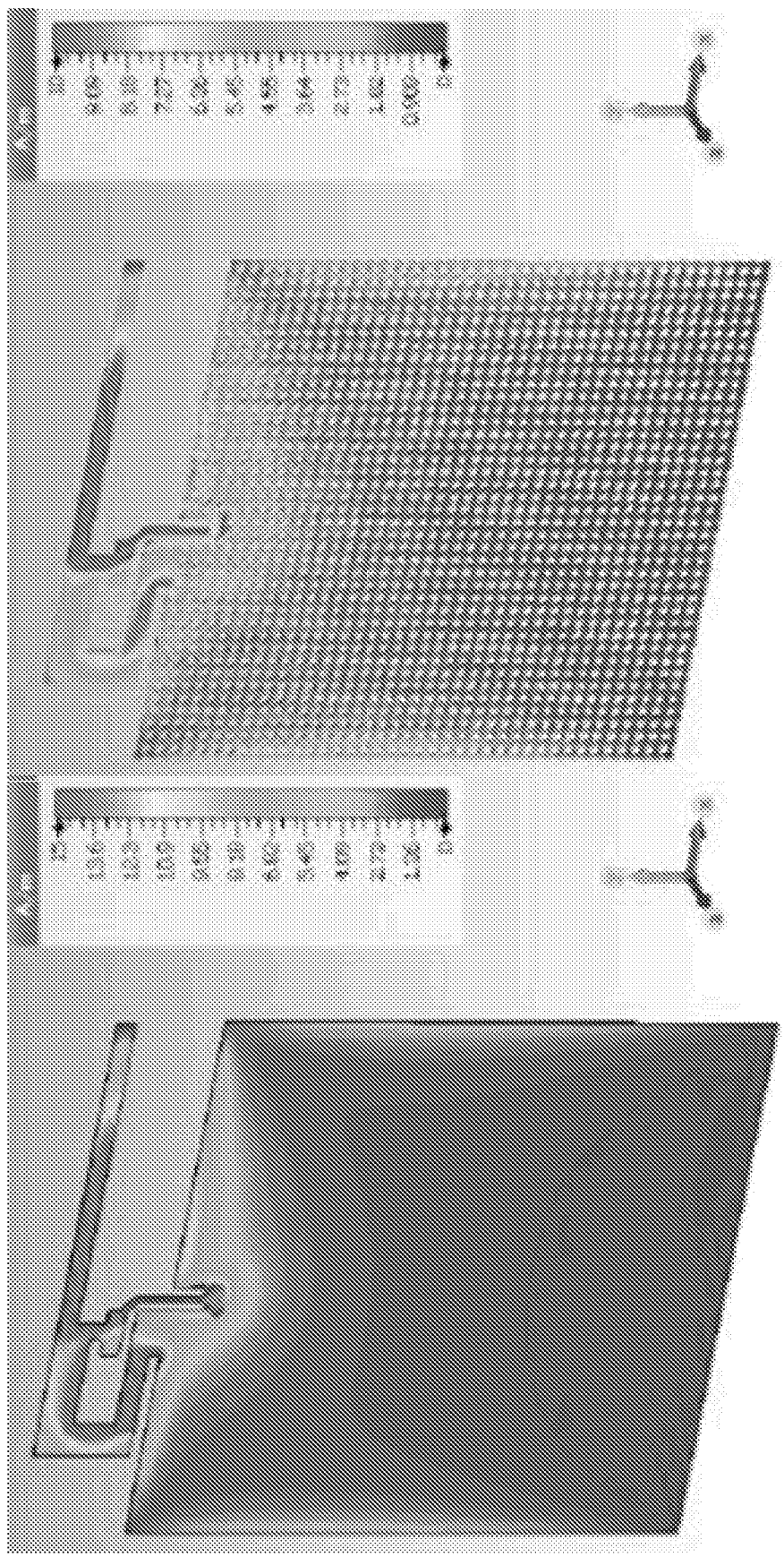
FIG. 6A shows a diagram depicting current distribution and radiation patterns results from simulations of an example IFA with a solid ground region.
FIG. 6B shows a diagram depicting the current distribution and radiation patterns results from simulations of an example IFA with a mesh ground region.

Radiation efficiency is a measure of the radiation of the antenna, taking heat loss into consideration. The efficiency is a ratio of power input vs. power output of the antenna. That can include energy lost due to heat or simply stored in the antenna due to it not radiating and rather resonating the energy. The smaller the footprint, the lower the heat dissipation, meaning most of the power radiated propagates with minimal loss thus achieving close to 100 percent efficiency. For example, the simulated radiation efficiency of the example IFA was approximately −0.175 dB. FIG. 6B shows a diagram depicting current distribution and radiation patterns results from simulations of an example IFA with mesh ground.

Equation 1 shows the relationship of radiated power and input power. In the equation, $P_{rad}$=Radiated power; $P_{in}$=Total Input Power$\eta$, $\eta_{cd}$=Radiation Efficiency, $\eta_c$=Conductive Efficiency, and $\eta_d$=Dielectric Efficiency.

$$P_{rad} = \eta_{cd} P_{in} \Longrightarrow \eta_{cd} = \frac{P_{rad}}{P_{in}} \quad \boxed{\eta = \eta_r \ \eta_c \ \eta_d} \quad \text{(Eq. 1)}$$

$$\frac{P_r}{P_t} = \frac{\eta_{cdt} \eta_{cdr}(1 - |\Gamma_t|^2)(1 - |\Gamma_r|^2)}{\left(\frac{\lambda}{4\pi R}\right)^2 D_t(\theta_t, \phi_t) D_r(\theta_r, \phi_r) |\hat{p}_t \cdot \hat{p}_r|^2} \quad \text{(Eq. 2)}$$

Radiation pattern illustrates the direction of radiation, for example, an isotropic antenna propagates equally in air all directions creating a spherically shaped radiation pattern. On the other hand, if the same antenna is placed on skin, the radiation pattern will distort due to skin conductivity property. For example, the dielectric of skin is 47, as compared to 1 for air, which slows the phase velocity in skin. Friis Transmission Equation shown below (Equation 2), calculates the antenna power received from an adjacent antenna transmitting at a known power ($P_t$) placed a distance of R from each other. In Equation 2, Pr=Radiated power; Pt=Transmitted Power; $\eta_{cd}$=Radiation efficiency; and D=Conductive Efficiency.

Gain is the normalized radiation with an ideal isotropic antenna. The simulated IFA gain was determined to be 2.539 dBi. Equation 3 shows the relationship of radiation intensity and power, where $P_{in}$=Total Input Power; and U=Radiation Intensity.

$$G(\theta, \phi) = 4\pi \frac{\text{Radiation Intensity}}{\text{Total Input Power}} = \frac{4\pi U(\theta, \phi)}{P_{in}} \quad \text{(Eq. 3)}$$

In the example study, the antenna back structure and feed design of the example IFA was optimized for impedance matching and radiation efficiency. The example antenna design used in the study is shown in FIG. 1B, e.g., flex-stretch IFA 100B. For example, the removal of small features from the ground plane (e.g., 100 times smaller than the wavelength) were designed to create the mesh structure. The mesh design was optimized according to the material composition and curvature of the surface to which the antenna structure would be applied. The design of the example embodiment of the IFA device is completely flexible, allowing conformity to any to other semi-flexible design shapes. The antenna and its environment was simulated with an HFSS simulation tool, as shown in FIG. 7. FIG. 7 shows plots from an example HFSS simulation showing the $S_{11}$ parameter matched at 2.4 GHz. The simulations also included a comparison between a solid ground and the mesh ground plane, which resulted in similar radiation patterns and current distribution, as shown in FIGS. 6A and 6B. The antenna dimensions of the example IFA device were 200 nm thick and 42.5 mm×35.6 mm, as shown in FIG. 1B. It is notable, for example, that the radiation pattern of the example IFA with mesh ground is similar to a dipole antenna simulated in HFSS over air.

Figure 8B:
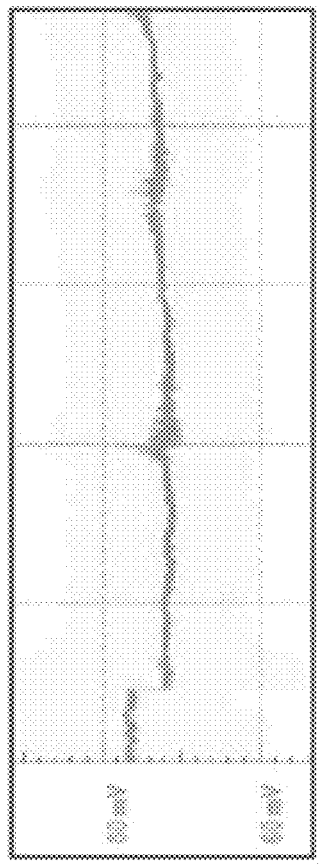
FIGS. 8B and 8C show plots of example EMG measurements from a subject's forearm in a relaxed state and flexed state, respectively.
Figure 8C:
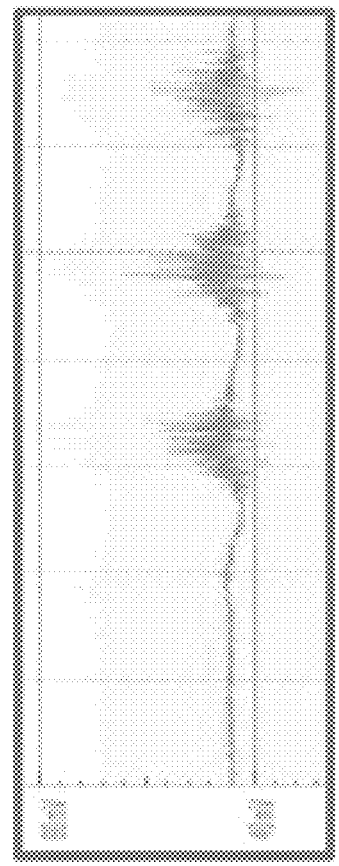
Figure 8A:
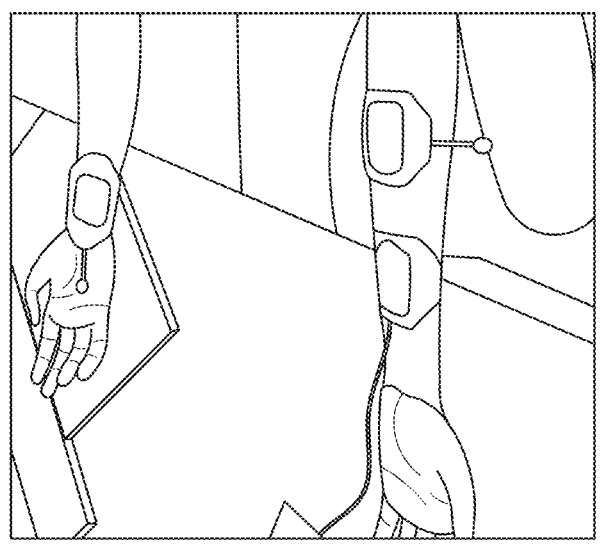
FIG. 8A shows an image of example EMG sensor created from the mesh structure of an example IFA device in accordance with the present technology.

The design of the IFA device can be optimized for different materials and curvature for different applications. The example design used in the study was fabricated and embedded within an FDA-approved, medical-grade skin adhesive tegaderm (3M, Tegaderm™). While adding the meshing characteristic added stretchability to the antenna, the mesh structure also allowed for the use as a physiological sensor to capture EMG when applied on skin, as shown in FIGS. 8A-8C. FIG. 8A shows an image of example EMG sensor created from the mesh structure of an example IFA device in accordance with the present technology. FIG. 8B shows a plot of example EMG measurements from a subject's forearm in a relaxed state, and FIG. 8C shows a plot of example EMG measurements from the subject's forearm in a flexed state (e.g., first closed).

The example IFA device was fabricated in accordance with the example manufacturing method of FIG. 2A. In implementations in the study, for example, the antenna was excited with 3 dBm of input power at 2.4 GHz. A spectrum analyzer was used to measure the power received via an off-the-shelf antenna while varying the distance and orientation. The power levels sensitivity received by the example IFA device was higher than what is needed to communicate with the Bluetooth module (e.g., −89 dBm). An RF system-level test was performed by connecting an example embodiment of the flexible antenna to a Bluetooth module to communicate to a smartphone over a range of 200 ft.

Figure 9:
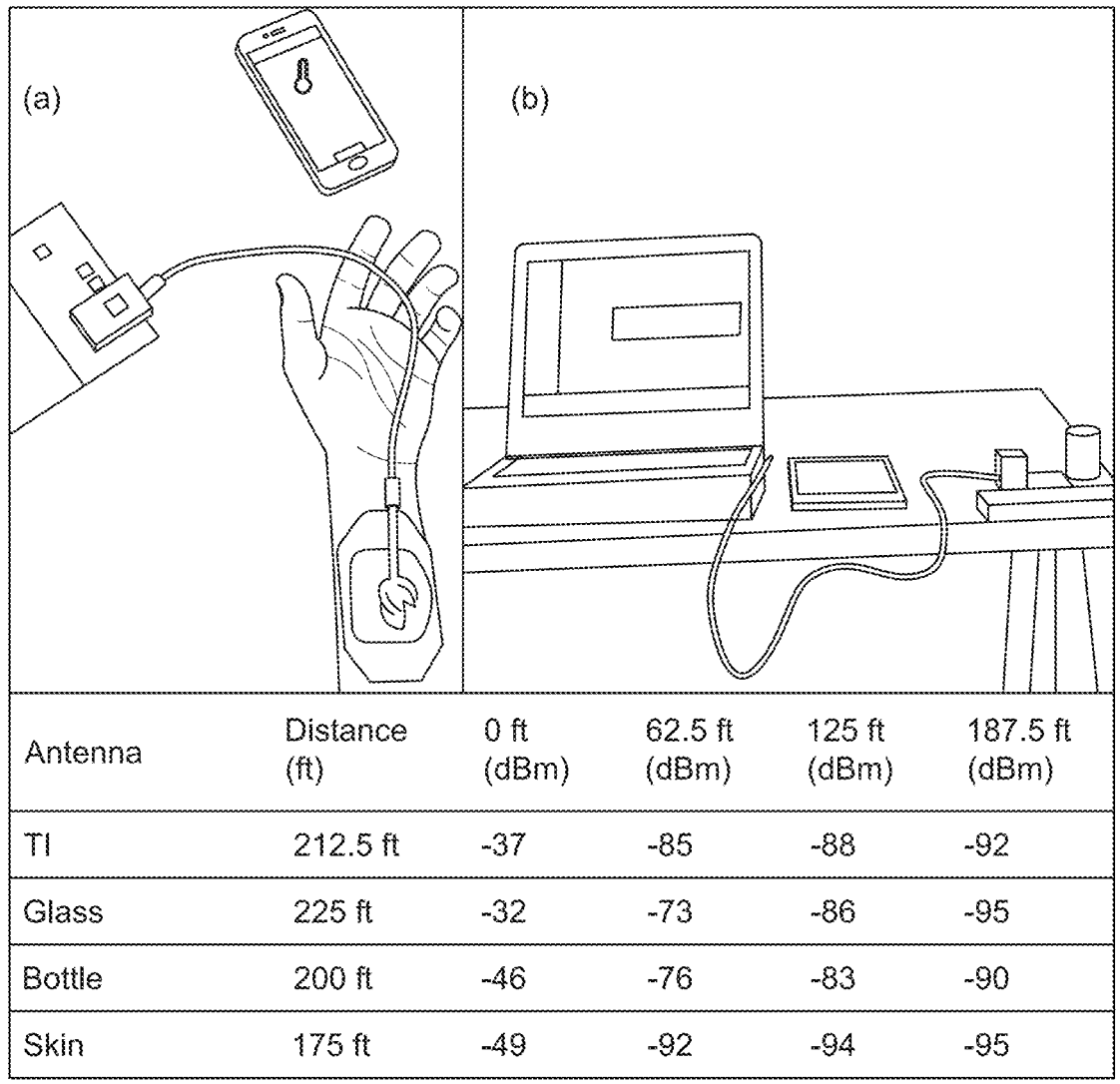
FIG. 9 shows a photo of the example RF system-level test setup and comparative results of an example flexible, stretchable antenna mounted on different materials or objects.

In the RF system-level test, for example, the example IFA antenna (employing an FDA-approved 3M Tegaderm™ adhesive) was attached to a subject's skin. The antenna was then connected to a BLE evaluation board (evb) via SMA cable. Firmware code was developed that enables the sensing of a switch counter which could be manually operated (e.g., operated once per second), as the digital signals were transmitted. The wireless system communicated to a smartphone via an iOS application that developed internally. The smartphone was held by an operator and moved away from the antenna setup down a long hallway. Communications using the flexible antenna were successful, e.g., up to 175 ft. Sensitivity measurements were also performed by measuring the change of power with respect to distance, using a BLE phone application. In addition, the same sensitivity measurements were carried out using a control (e.g., an off-the-shelf TI antenna) connected to the same evaluation board. FIG. 9 shows a photo of the example RF system-level test setup (in panels (a) and (b)), and example comparative results of the flexible antenna mounted on different materials or objects, including glass, plastic and skin.

Figure 10:
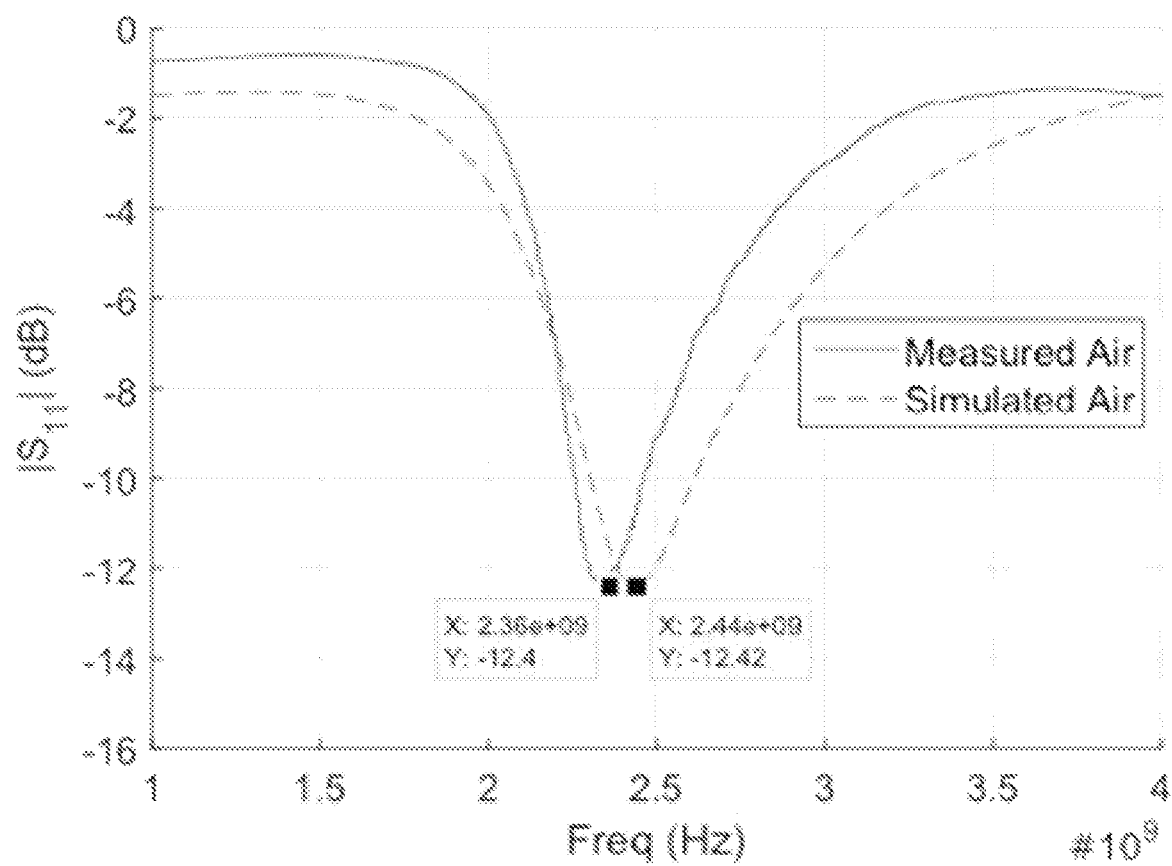
FIG. 10 shows a plot depicting measured and simulated reflected power values of an example IFA.

Measurements of the IFA device were performed and compared to the simulated results. For example, using a network analyzer calibrated for one port, the example IFA reflected power $|S_{11}|$ propagating over air at 2.4 GHz was measured to be −12 dB. These measured results closely matched the simulated results, as shown in FIG. 10. FIG. 10 shows a plot depicting the measured and simulated reflected power of an example IFA.

Figure 11B:
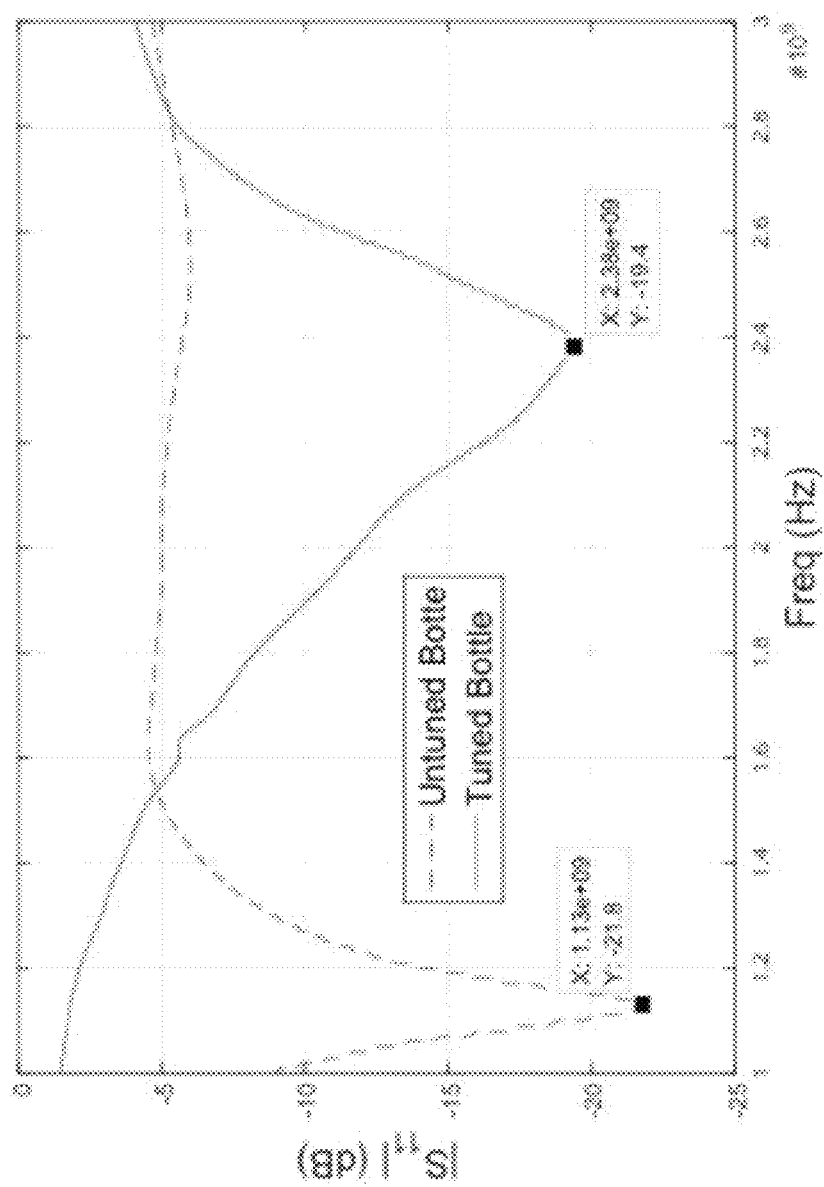
FIG. 11B shows a plot depicting t measured and simulated reflected power values of an example flexible antenna, stretchable mounted on the bottle and tuned to 2.4 GHz.
Figure 11A:
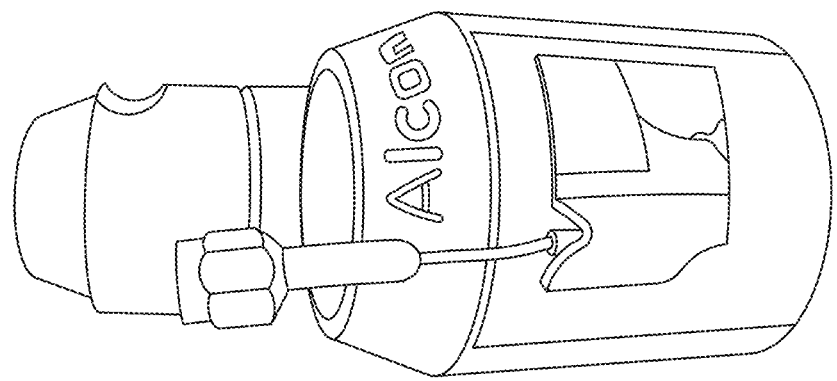
FIG. 11A shows an image of an example flexible, stretchable antenna in accordance with the present technology attached to a bottle.

The IFA design was also simulated and measured on a bottle filled with saline, as well as skin. FIG. 11A shows an image of an example flexible antenna in accordance with the present technology attached to a bottle (e.g., medicinal bottle). FIG. 11B shows a plot depicting the $S_{11}$ measured using a network analyzer once the example IFA was mounted on the bottle and tuned to 2.4 GHz. Initially the example flexible antenna was radiating at −21 dB at 1.1

GHz. The antenna on the bottle was tuned by simply cutting the fork of the antenna using scissors. For example, this enables customized tuning to a desired frequency, e.g., from 1.1 GHz to the target in this example implementation of 2.4 GHz for BLE application. The $S_{11}$ of the antenna at 2.4 GHz was measured to be −19 dB.

In the case of air, for example, $v_{phase}$ (velocity) and c (speed of light) are the same value as phase both permittivity and permeability are 1 hence f=λ/c. In the case of the bottle, for example, the permittivity is around 4. Therefore the $v_{phase}$ is half the speed of light (c/2). The derivation below demonstrates the wavelength over the speed of light results in half the frequency on a bottle compared to air, f/2=λ/c. This derivation is consistent with the measured results shown. When the medium changes from air to bottle, the frequency shifted from 2.4 GHz to 1.2 GHz as expected. For example:

$$v_{phase}=c/\sqrt{(\varepsilon_r^* \mu_r)}=c/2 \text{(case of bottle } \varepsilon_r=4,\mu=1) \quad \text{(Eq. 4)}$$
$$\Rightarrow v_{phase}=\lambda/f=c/2$$
$$\Rightarrow F=\lambda/v_{phase}=\lambda/(c/2)=2\lambda/c \Rightarrow f/2=\lambda/c$$

As such, the antenna can be customized to operate at a desired frequency and on a desired object.

Figure 12A:
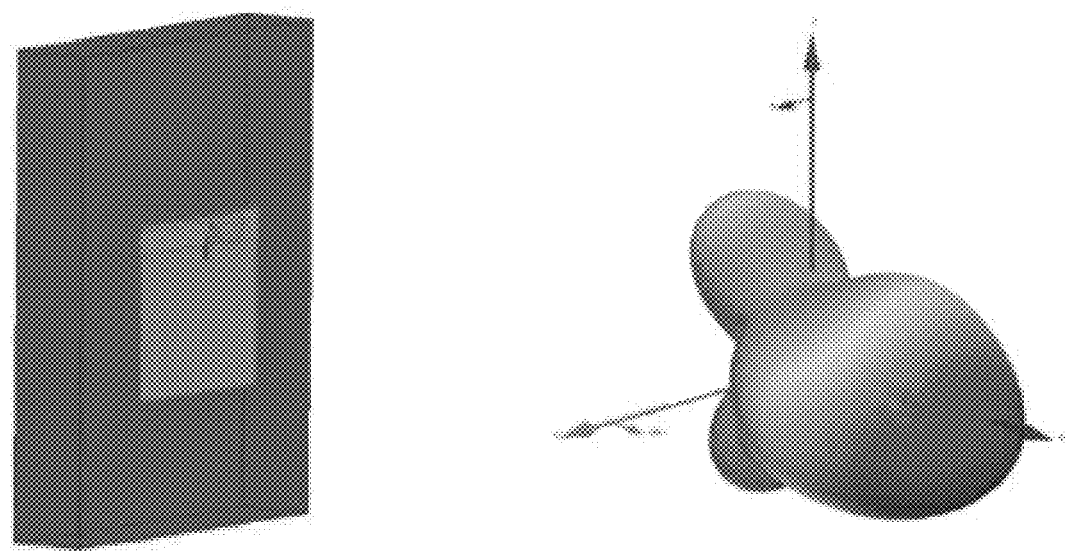
FIG. 12A shows a 3D schematic and radiation pattern simulation of an example IFA on skin.

The example IFA was simulated on skin. Example results of the simulation showed the radiation pattern was altered due to significant amounts of skin absorption, as depicted in FIG. 12A. FIG. 12A shows a 3D schematic and radiation pattern simulation of an example IFA on skin. In the simulation, the antenna displayed significant amount of capacitive coupling to the body. The antenna's near field profile is drastically affected due to its proximity to the human tissue. The radiation of the antenna is dependent on the location of the antenna and different body types, e.g., muscular, skinny or fat. Table 8 presents permittivity and conductivity values of various body tissues and wearable materials.

TABLE 8

| Material | Permittivity | Conductivity |
|---|---|---|
| Air | 1.0 | 0.00 |
| Skin | 46.8 | 0.69 |
| Fat | 5.6 | 0.04 |
| Cortical bone | 13.2 | 0.09 |
| Cancellous | 22.4 | 0.18 |
| Muscle | 57.1 | 0.8 |
| Blood | 64.0 | 1.35 |
| Epoxy | 4.4 | 0.00004 |
| Glass | 5.5 | 0 |
| Alumina | 9.6 | 0.000014 |

Figure 12B:
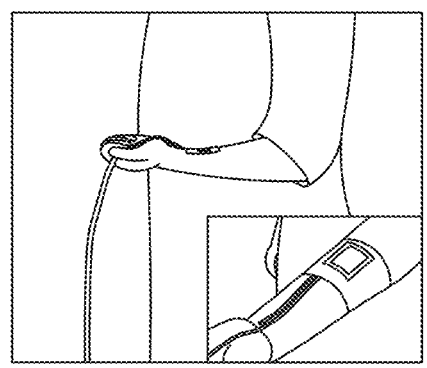
FIG. 12B shows an image of the example IFA antenna on the subject's skin in the anechoic chamber and 2D radiation pattern measurements in the chamber.
Figure 12B:
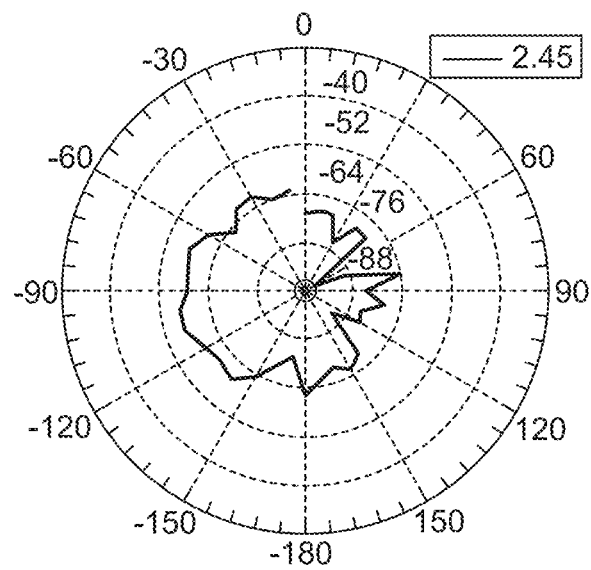

Human tissue exhibits very glossy, inefficient mediums to propagate radio frequency. In the example study, the flexible, stretchable antenna device was mounted on a subject's skin and the radiation pattern at 2.4 GHz was measured in an anechoic chamber, as shown in FIG. 12B. FIG. 12B shows an image of the example IFA antenna on the subject's skin in the anechoic chamber and 2D radiation pattern measurements in the chamber.

Figure 13:
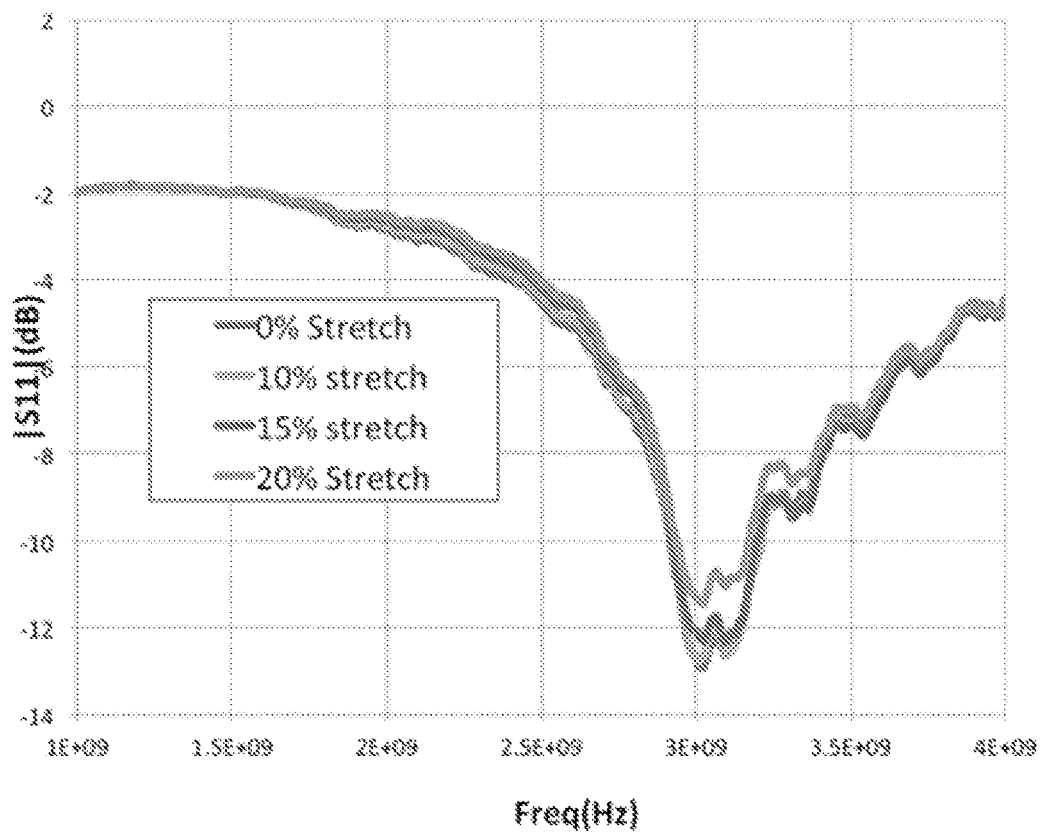
FIG. 13 shows a plot depicting measured $S_{11}$ values for an example flexible, stretchable antenna under varying degrees of stretching.

Stretching tests were performed in the study, e.g., to test the performance of the antenna under various stretching conditions. An example flexible was placed into a mechanical device designed to apply opposing forces to the product, stretching it to various lengths, e.g., in the Y-axis. The example antenna was connected to a network analyzer measuring the variation of the $S_{11}$ parameters due to stretching effect. The antenna was stretched under two conditions. In the first condition, for example, both the solid gold IFA and its meshed ground plane component were subjected to forces with the purpose of stretch testing the full antenna. The example IFA remained functional up to 120% of original product length before the solid gold of the example IFA cracked under testing. Similarly, as the antenna was stretched, the frequency remained the same while the gain shifted by 2 dB. Moreover, the example IFA propagated in air, and the variation of dielectric introduced by the test bed caused the frequency to shift from 2.4 GHz to 3 GHz as shown in FIG. 13. FIG. 13 shows a plot depicting measured $S_{11}$ values for an example flexible antenna under varying degrees of stretching.

Figure 14:
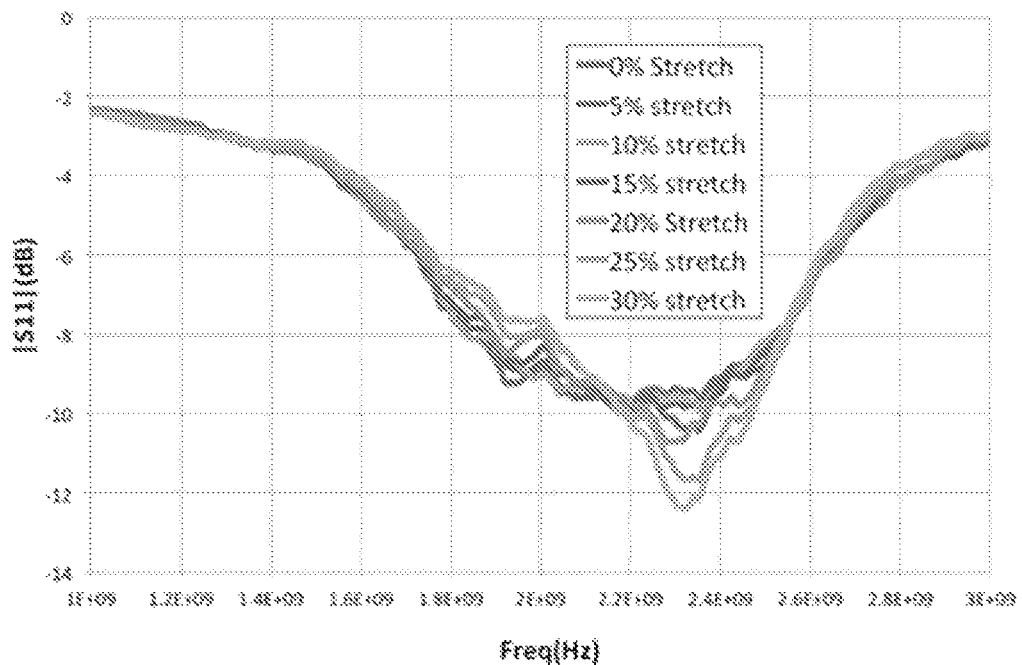
FIG. 14 shows a plot depicting measured $S_{11}$ values for an example flexible, stretchable antenna where the mesh region of the antenna was stretched under varying degrees of stretching.

For the second condition, for example, the example IFA remained clamped between two plastic vice grips with a high dielectric. The example IFA was simply tuned to 2.4 GHz by simply cutting the fork of the antenna using scissors. In this instance, the meshed ground plane alone experienced stretch test forces. Measurements were taken at increments of 5% from 105% to 130% of the product original length. The mesh design of the ground plane remained fully functional throughout this process. There was no variation in frequency due to stretching, resulting in an increase of the gain by 2 dB seen, as shown in FIG. 14. FIG. 14 shows a plot depicting measured $S_{11}$ values for an example flexible antenna where the mesh region of the antenna was stretched under varying degrees of stretching.

Exemplary implementations included stretching the example IFA in both the x-direction and the y-direction, independently, and in both directions at the same time. Example results of the implementations showed that the example IFA was stretchable up to about 200% in the y-direction and about 100% in the x-direction. The structure of the flex-stretch antenna 100 provides for desired stretching in multi-dimensions while maintaining the desired transmission capabilities and electrical radiofrequency performance of the antenna. For example, the flex-stretch antenna 100 can be stretched to a degree that matches that of skin.

Figure 15:
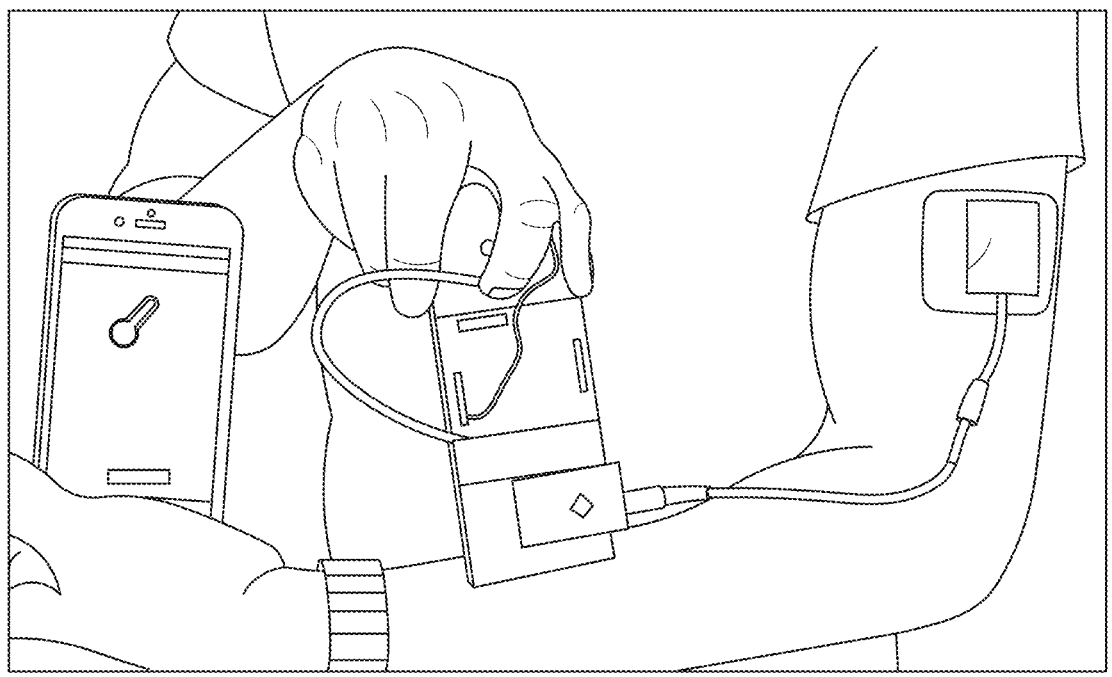
FIG. 15 shows an image of a system level test setup including an example flexible, stretchable antenna in communication with a smartphone.

The exemplary implementations included a system level test in the study to demonstrate a fully working system. The example flexible antenna (e.g., on an FDA-approved 3M Tegaderm™ adhesive) was attached to a subject's skin (e.g., directly to the bicep). The bicep was flexed intensively and repeatedly, leading the antenna to flex and stretch. The antenna was connected via an SMA cable to a BLE evaluation board. FIG. 15 shows an image of the system level test setup, including the example flexible antenna attached to the subject's bicep and connected to the BLE evaluation board, as well as the example app operating on the smartphone. The board firmware was programmed so that every time the switch onboard was engaged manually, it would increment the counter on the iOS app. Communications between the example flexible antenna and the smartphone over 150 ft apart from each other.

The results of the example system level test of the study showed a robust and successful implementation of the example flex-stretch IFA embedded on an FDA-approved adhesive that overcomes the challenges associated with transmitting detectable biomedical signals (e.g., electrophysiological, electrochemical or other biomedical signals) while in contact with skin, e.g., allowing for simultaneous recording and transmission in biomedical monitoring. For example, the challenges associated with conventional antenna designs includes the coupling of the body tissue which tends to act as a sponge, absorbing the transmitted signals and therefore hindering the fundamental purpose of the antenna, which is to propagate the signal outwards to a receiving device through the propagation medium (e.g., air).

In an example use case, a patient can be outfitted with the antenna, which is connected to a BLE transceiver, e.g., on a smartphone. The smartphone includes a customized smartphone application that is paired with the transceiver. In this situation, the example flex-stretch antenna was shown to propagate up to 175 ft away, including when the patient is moving or stationary (e.g., lying in bed). For example, the smartphone application can utilize a BLE protocol that provides built-in data security features in accordance with rules and regulations for medication compliance applications, e.g., based on FDA and HIPAA requirements.

Another example use case includes applicability to self-monitoring whereby the example flex-stretch antenna is placed into the subject's pocket with the subject placing a hand over it, in direct physical contact, in an effort to hamper propagation. The smartphone was shown to remain capable to communicate continuously with the example flex-stretch antenna. Moreover, the example flex-stretch antenna includes a structure where the ground component is meshed so that it can be vigorously stretched, e.g., simulating the similar characteristics of skin, and yet still be able to transmit effectively. Furthermore, this example structural design of the flex-stretch antenna was shown to provide multi-functionality of the device as an 'electenna', where the electenna's ground component served as a ground for the antenna and a sensor detecting electrophysiological signals, simultaneously. For example, the electenna was shown to capture EMG signals during transmission.

EXAMPLES

In an example embodiment of a flexible and stretchable antenna device (example A1), the antenna device includes an adhesive substrate having flexible and stretchable material properties and structured to adhere to a surface of an object; and an antenna coupled to the adhesive substrate, the antenna including a radiating antenna part and an antenna ground part that operate to transmit or receive a wireless communication signal, in which the antenna ground part includes a mesh structure allowing the antenna to transmit or receive the wireless communication signal at a predetermined operating frequency while being stretched.

Example A2 includes the antenna device of example A1, in which the antenna includes a structural layout configured as an inverted F antenna (IFA).

Example A3 includes the antenna device of example A2, in which the IFA is structured to include the radiating antenna part having a terminal end that aligns with one end side of the antenna ground part, and the antenna ground part having a substantially rectangular geometry.

Example A4 includes the antenna device of example A2, in which the IFA includes an antenna feed part that extends from proximate the radiating antenna part into a void region of the antenna ground part without making contact with the antenna ground part to interface with an electrical circuit or electronic device on the adhesive substrate.

Example A5 includes the antenna device of example A2, in which the IFA includes a mark on one or both of the antenna and the adhesive substrate indicating a line to cut the antenna device to remove a portion of the antenna device and thereby modify the antenna device such that a user can define an operating frequency of the modified antenna device.

Example A6 includes the antenna device of example A5, in which the mark is oriented on the antenna device based on a second predetermined operating frequency different than the first predetermined operating frequency associated with the object.

Example A7 includes the antenna device of example A2, in which the IFA is electrically connected to one or more sensors to measure at least one of electromyography (EMG) signals, electrocardiography (EKG), electroencephalography (EEG) signals, electrogastrography (EGG), electrooculography (EOG), electrochemical signals, temperature measurements, humidity measurements, pressure measurements, motion, or location.

Example A8 includes the antenna device of example A2, in which the antenna ground part of the IFA includes an array of electrodes formed in the mesh structure.

Example A9 includes the antenna device of example A8, in which electrodes in the mesh structure are configured to collect physiological signals from a living subject while simultaneously transmitting the collected physiological signals in the wireless communication signal at the predetermined operating frequency.

Example A10 includes the antenna device of example A9, in which the collected physiological signals include one or more of electromyography (EMG) signals, electrocardiography (EKG), electroencephalography (EEG) signals, electrogastrography (EGG), electrooculography (EOG), electrochemical signals, temperature measurements, or humidity measurements.

Example A11 includes the antenna device of example A8, in which electrodes in the mesh structure are configured to collect data pertaining to use of a medical treatment container.

Example A12 includes the antenna device of example A11, in which the collected data includes a detection of an external contact with or motion of the surface to which the antenna device is adhered.

Example A13 includes the antenna device of example A1, in which the object is a living subject, and the surface to adhere the flexible and stretchable antenna device is skin of the living subject.

Example A14 includes the antenna device of example A1, in which the object is a non-animate object.

Example A15 includes the antenna device of example A14, in which the surface of the non-animate object to adhere the flexible and stretchable antenna device includes one or more of a plastic or a glass.

Example A16 includes the antenna device of example A1, in which the adhesive substrate includes a medical-grade adhesive material.

Example A17 includes the antenna device of example A16, in which the medical grade adhesive material includes tegaderm.

Example A18 includes the antenna device of example A1, in which the adhesive substrate includes a heat and moisture resistant material.

Example A19 includes the antenna device of example A18, in which the heat and moisture resistant material includes a polyamide film.

Example A20 includes the antenna device of example A1, in which the antenna includes a metal film including at least one of gold or chromium.

Example A21 includes the antenna device of example A1, in which the antenna device is configured to be stretchable of at least 50% in multiple directions.

Example A22 includes the antenna device of example A1, in which the mesh structure includes an array of features interleaved with openings, the features having a size smaller than the wavelength associated with the wireless communication signal at the predetermined operating frequency.

Example A23 includes the antenna device of example A1, in which the radiating antenna part includes the mesh structure.

In an example embodiment of a device (example A24), the device includes an adhesive substrate having flexible and stretchable material properties and structured to adhere to a surface of an object; and an antenna coupled to the adhesive substrate and including (1) a mesh of structures and openings that are interleaved to transmit or receive a wireless communication signal at a predetermined operating frequency while being stretched, and (2) an array of sensing electrodes formed in the mesh of the antenna to sense a detectable attribute of the object as a detected signal while simultaneously transmitting the detected signal in the wireless communication signal at the predetermined operating frequency.

Example A25 includes the device of example A24, in which the electrodes in the mesh include square regions positioned between serpentine interconnections.

Example A26 includes the device of example A24, in which electrodes in the mesh are configured to collect physiological signals from a living subject while simultaneously transmitting the collected physiological signals at the predetermined operating frequency.

Example A27 includes the device of example A26, in which the collected physiological signals include one or more of electromyography (EMG) signals, electrocardiography (EKG), electroencephalography (EEG), electrogastrography (EGG), or electrooculography (EOG) signals.

Example A28 includes the device of example A24, in which electrodes in the mesh are configured to collect data pertaining to use of a medical treatment container.

Example A29 includes the device of example A28, in which the collected data includes a detection of an external contact with or motion of the surface to which the device is adhered.

Example A30 includes the device of example A24, in which the device includes a mark on one or both of the antenna and the adhesive substrate indicating a line to cut the device to remove a portion of the antenna and thereby modify the antenna such that a user can define an operating frequency of the modified antenna.

Example A31 includes the device of example A30, in which the mark is oriented on the device based on a second predetermined operating frequency different than the first predetermined operating frequency associated with the object.

In an example embodiment of a health monitoring system (example A32), the system includes an antenna device capable of being flexed and stretched while transmitting or receiving a wireless communication signal at a particular operating frequency, the antenna device including an adhesive substrate structured to be flexible and stretchable and capable of adhering to a surface of a target including a living subject or an inanimate object associated with a medical treatment of a patient user, and an antenna coupled to the adhesive substrate, the antenna including a radiating antenna part and an antenna ground part, in which the antenna ground part includes a mesh structure including an array of features and interleaved openings, the features having a size smaller than the wavelength associated with the wireless communication signal at the predetermined operating frequency; a sensor to detect signal data associated with a detectable attribute of the target; an electronics unit including a signal conditioning unit and a transceiver unit, the signal conditioning unit to amplify and filter the detected signal data, and the transceiver unit to regulate transmission of the wireless communication signal by the antenna device; and a wireless receiver device to receive transmitted wireless communication signals from the antenna device at the predetermined operating frequency.

Example A33 includes the system of example A32, in which the antenna includes a structural layout configured as an inverted F antenna (IFA).

Example A34 includes the system of example A31, in which the antenna device includes a mark on one or both of the antenna and the adhesive substrate indicating a line to cut the antenna device to remove a portion of the antenna device and thereby modify the antenna device such that a user can define an operating frequency of the modified antenna device.

Example A35 includes the system of example A31, in which the wireless receiver device includes a mobile device including a software application operable on the mobile device and comprising instructions stored in a memory and processed by a processor of the mobile device, the mobile device including a wireless communications unit to receive the wireless communications signal from the antenna device.

Example A36 includes the system of example A35, in which the mobile device includes at least one of a smartphone, a tablet, or a wearable device including a smartwatch or a smartglasses.

Example A37 includes the system of example A35, further including one or more computers in communication with the mobile device over the Internet, the one or more computers including a memory to store detected signal data received from the antenna device, and a processor to process the detected signal data.

Example A38 includes the system of example A31, in which the sensor includes electrodes integrated with the antenna ground part, the electrodes formed in the mesh structure and configured to collect physiological signals from the living subject while simultaneously transmitting the collected physiological signals in the wireless communication signal at the predetermined operating frequency to the wireless receiver device, or collect data from the inanimate object pertaining to use of the inanimate object.

Example A39 includes the system of example A38, in which the collected data from the inanimate object includes a detection of an external contact with or motion of the surface to which the antenna device is adhered.

Example A40 includes the system of example A31, in which the predetermined operating frequency includes a frequency used by a standard wireless communications protocol including one or more of Bluetooth, Bluetooth Low Energy (BLE), Wi-Fi, or a cellular communications standard.

In an example embodiment of a method of fabricating a flexible and stretchable antenna (example A41), the method includes applying a thin sheet layer of a heat and moisture resistive material to a rigid substrate that is covered with a peelable material; depositing a thin metal film over the thin sheet layer on the peelable material covered on the rigid substrate; forming an antenna structure by performing one or both of photolithography and wet etching of the thin metal film, the antenna structure formed on the thin sheet layer and structured to include a radiating antenna part and an antenna ground part, in which one or both of the radiating antenna part and the antenna ground part include a mesh structure to allow the antenna structure to undergo stretching; and producing an antenna device that is flexible and stretchable by transferring the formed antenna structure on the thin sheet layer to a flexible and stretchable adhesive material.

Example A42 includes the method of example A41, in which the transferring includes peeling off the antenna structure on the thin sheet layer from the rigid substrate.

Example A43 includes the method of example A42, in which the peeling off includes attaching an intermediary adhesive material on the exposed side of the antenna structure attached to the thin sheet layer, in which the opposite side of the exposed side releases from the rigid substrate; attaching the flexible and stretchable adhesive material to the opposite side, in which the thin sheet layer material contacts the flexible and stretchable adhesive material; and removing the intermediary adhesive material.

Example A44 includes the method of example A43, in which the removing the intermediary adhesive material includes dissolving the intermediary adhesive material.

Example A45 includes the method of example A41, further including tuning the antenna structure to meet a target radio frequency (RF) performance.

Example A46 includes the method of example A45, in which the tuning includes removing a predetermined portion of the antenna device to modify the antenna structure such that the antenna device will operate at the target RF performance.

Example A47 includes the method of example A46, in which the predetermined portion is indicated by a mark on one or both of the antenna structure and the adhesive material indicating a line to cut the antenna device for the removing.

Example A48 includes the method of example A41, in which the heat and moisture resistive material includes a polyamide film material.

Example A49 includes the method of example A48, in which the polyamide film material includes Kapton.

Example A50 includes the method of example A41, in which the peelable material includes polydimethylsiloxane (PDMS).

Example A51 includes the method of example A41, in which the rigid substrate includes glass.

Example A52 includes the method of example A41, in which the thin metal film includes at least one of gold or chromium.

In an example embodiment of a method of producing an antenna (example A53), the method includes providing a flexible and stretchable antenna attached on or at least partially embedded within an adhesive substrate, the antenna including a radiating antenna part and an antenna ground part, in which one or both of the radiating antenna part and the antenna ground part include a mesh structure allowing the antenna to transmit or receive a wireless communication signal at a first predetermined operating frequency while being stretched; and tuning a transmission frequency of the flexible and stretchable antenna, in which tuning includes removing a portion of at least the radiating antenna part to modify cause the antenna to transmit or receive at a second operating frequency.

Example A54 includes the method of example A53, in which the portion is indicated by a mark on one or both of the antenna and the adhesive substrate indicating a line to cut the antenna device for the tuning.

Example A55 includes the method of example A54, in which one or both of the antenna and the adhesive substrate include a label proximate the mark indicative of the second operating frequency.

Example A56 includes the method of example A54, in which one or both of the antenna and the adhesive substrate include a second mark indicating a second line to cut the antenna device for the tuning to a third operating frequency.

Example A57 includes the method of example A56, in which one or both of the antenna and the adhesive substrate include a second label proximate the mark indicative of the third operating frequency.

In an example embodiment of a method of fabricating an antenna (example B1), the method includes applying a thin sheet of a heat and moisture resistive material to a rigid substrate that is covered with a peelable material; depositing a thin metal film over the thin sheet and the rigid substrate; forming an antenna structure by performing photolithography and wet etching of the thin metal film; and peeling off the antenna structure from the rigid substrate.

Example B2 includes the method of example B1, further including tuning the antenna structure to meet a target radio frequency (RF) performance.

Example B3 includes the method of example B1 in which the heat and moisture resistive material includes a polyamide film material.

Example B4 includes the method of example B1, in which the polyamide film material includes Kapton.

Example B5 includes the method of example B1, in which the peelable material includes polydimethylsiloxane (PDMS).

Example B6 includes the method of example B1, in which the rigid substrate includes glass.

Example B7 includes the method of example B2, in which the tuning includes estimating an initial tuning frequency of the antenna structure; and selectively re-tuning the initial tuning frequency to meet a target tuning frequency by trimming and removing material from the antenna structure.

In an example embodiment of an inverted F radio frequency antenna (RF-IFA) device (example B8), the RF-IFA device includes a first layer made up of a flexible and peelable material; a second insulating layer over the first layer made up of a heat and moisture resistant material; and a thin metal film layer over the second insulating layer, the thin metal film layer being shaped to resemble an inverted F shape.

Example B9 includes the RF-IFA device of example B8, in which the flexible and peelable material includes polydimethylsiloxane (PDMS).

Example B10 includes the RF-IFA device of example B8, in which the heat and moisture resistant material includes a polyamide film.

Example B11 includes the RF-IFA device of example B8, in which the thin metal film layer includes a Chromium or Gold (Cr/Au) film having a thickness between 10 to 200 nm.

Example B12 includes the RF-IFA device of example B8, in which the RF-IFA device further includes an antenna port at which an external electronic circuit can be coupled to the RF-IFA device to measure an RF signal received by the RF-IFA device.

In an example embodiment of an inverted F antenna (example C1), the inverted F antenna includes a ground plane including a mesh structure; an active region coupled to the ground plane, the active region including an upper arm including a radiating element configured to resonate for transmission at a transmission frequency, in which the inverted F antenna includes an initial length and is configured to be flexible and stretchable, the inverted F-antenna being configured to be capable of being stretched up to 150% of the initial length while maintaining transmission at the transmission frequency.

Example C2 includes the antenna of example C1, in which the antenna is configured to be at least as stretchable as human skin.

Example C3 includes the antenna of example C1, in which the active region includes the mesh structure.

Example C4 includes the antenna of example C1, in which the mesh structure includes a plurality of squares and interconnecting serpentine bridges.

Example C5 includes the antenna of example C1, in which the mesh structure includes a plurality of serpentine bridges.

Example C6 includes the antenna of example C1, in which the antenna is configured to maintain transmission at 2.4 GHz.

Example 7C includes the antenna of example C1, in which the inverted F antenna includes a metal film including at least one of gold and chromium.

Example C8 includes the antenna of example C1, in which the ground plane region includes a plurality of sensors.

Example C9 includes the antenna of example C8, in which the plurality of sensors includes at least one of electrocardiography (ECG), electromyography (EMG), electrogastrography (EGG), and electroencephalography (EEG) measurements.

Example C10 includes the antenna of example C8, in which the plurality of sensors includes at least one of a humidity sensor, a pressure sensor, a temperature sensor, a motion sensor and a location sensor.

In an example embodiment of an assembly (example C11), the assembly includes an adhesive configured to adhere to a surface; and an antenna assembly adhered to the adhesive, in which the antenna assembly is configured to be positioned between the adhesive and the surface, in which the antenna assembly includes a metal film inverted F antenna, and in which the metal film inverted F antenna includes a mesh structure, the metal film inverted F antenna being configured to stretch up to 150% of an initial length while maintaining a transmission frequency.

Example C12 includes the assembly of example C11, in which the transmission frequency is 2.4 GHz.

Example C13 includes the assembly of example C11, in which metal film inverted F antenna is configured to be at least as stretchable as human skin.

Example C14 includes the assembly of example C11, in which the metal film inverted F antenna includes an active region and a ground plane, the ground plane including the mesh structure.

Example C15 includes the assembly of example C14, in which the active region includes the mesh structure.

Example C16 includes the assembly of example C11, in which the mesh structure includes a plurality of squares and interconnecting serpentine bridges.

Example C17 includes the assembly of example C11, in which the mesh structure includes a plurality of serpentine bridges.

Example C18 includes the assembly of example C11, in which the adhesive includes a medical grade adhesive configured for positioning on human skin.

Example C19 includes the assembly of example C11, in which the adhesive is configured for positioning on.

Example C20 includes the assembly of example C11, in which the antenna assembly includes a heat and moisture resistant layer, in which the metal film inverted F antenna is between the moisture resistant layer and the adhesive.

Example C21 includes the assembly of example C20, in which the heat and moisture resistant layer includes polyimide.

Example C22 includes the assembly of example C11, in which the metal film inverted F antenna includes a ground plane region including a plurality of sensors.

Example C23 includes the assembly of example C22, in which the plurality of sensors includes at least one of a humidity sensor, a pressure sensor, a temperature sensor, a motion sensor and a location sensor.

Example C24 includes the assembly of example C22, in which the plurality of sensors includes at least one of electrocardiography (ECG), electromyography (EMG), electrogastrography (EGG), and electroencephalography (EEG) measurements.

Example C25 includes the assembly of example C24, in which the adhesive includes medical grade adhesive configured to be positioned on human skin and in which the metal film inverted F antenna including the plurality of sensors is configured to be in direct contact with the human skin while the assembly is positioned on the human skin.

Example C26 includes the assembly of example C25, further including a heat and moisture layer, in which the heat and moisture layer is between the metal film inverted F antenna and the adhesive.

In an example embodiment of a method of fabricating an antenna (example C27), the method includes providing a flexible and stretchable inverted F antenna including an upper arm having a first length, the upper arm being coupled to a ground plane, and the ground plane including a mesh structure; and tuning a transmission frequency of the inverted F antenna, in which tuning the transmission frequency includes shortening the upper arm from the first length to a second shorter length.

Example C28 includes the method of example C27, in which providing the flexible and stretchable inverted F antenna includes providing at least one tuning marker on the inverted F antenna, and in which tuning the transmission frequency includes removing a portion of the upper arm based on the tuning marker on the inverted F antenna.

Example C29 includes the method of example C28, in which providing the at least one tuning marker includes providing the at least one tuning marker on the upper arm of the inverted F antenna.

Example C30 includes the method of example C27, in which providing the flexible and stretchable inverted F antenna includes providing an assembly including the flexible and stretchable inverted F antenna.

Example C31 includes the method of example C30, in which providing the flexible and stretchable inverted F antenna includes providing at least one tuning marker on the assembly, and in which tuning the transmission frequency includes removing a portion of the upper arm based on the tuning marker on the assembly.

Example C32 includes the method of example C30, in which providing the assembly includes providing the flexible and stretchable inverted F antenna adhered to an adhesive.

Example C33 includes the method of example C32, in which the adhesive includes a medical grade adhesive configured for positioning on human skin.

Example C34 includes the method of example C32, in which the adhesive is configured for positioning on a nonorganic surface.

Example C35 includes the method of example C32, in which the assembly includes a heat and moisture resistant layer, in which the metal film inverted F antenna is between the moisture resistant layer and the adhesive.

Example C36 includes the method of example C35, in which the heat and moisture resistant layer includes polyimide.

Example C37 includes the method of example C27, in which providing the flexible and stretchable inverted F antenna includes providing an inverted F antenna including a ground plane including a plurality of sensors.

Example C38 includes the method of example C37, in which the plurality of sensors includes at least one of a humidity sensor, a pressure sensor, a temperature sensor, a motion sensor and a location sensor.

Example C39 includes the method of example C37, in which the plurality of sensors includes at least one of electrocardiography (ECG), electromyography (EMG), electrogastrography (EGG), and electroencephalography (EEG) measurements.

Example C40 includes the method of example C27, in which providing the flexible and stretchable inverted F antenna includes providing an antenna configured to transmit at a frequency of 2.4 GHz.

Example C41 includes the method of example C27, in which providing the flexible and stretchable inverted F antenna includes providing an antenna configured to stretch up to 150% of an initial length.

Example C42 includes the method of example C27, in which providing the flexible and stretchable inverted F antenna includes providing an antenna configured to be at least as stretchable as human skin.

Example C43 includes the method of example C27, in which the active region includes the mesh structure.

Example C44 includes the method of example C37, in which the mesh structure includes a plurality of squares and interconnecting serpentine bridges.

Example C45 includes the method of example C37, in which the mesh structure includes a plurality of serpentine bridges.

In an example embodiment of a method of fabricating an antenna (example C46), the method includes providing a thin sheet of a heat and moisture resistant material over a substrate covered with a weakly-adhesive material; depositing a thin metal film over the weakly-adhesive material; patterning the thin metal film to form an inverted F antenna including a mesh structure.

Example C47 includes the method of example C46, in which the inverted F antenna includes an active region and a ground plane, and in which the ground plane includes the mesh structure.

Example C48 includes the method of example C47, in which the active region includes the mesh structure.

Example C49 includes the method of example C46, in which the mesh structure includes a plurality of squares and interconnecting serpentine bridges.

Example C50 includes the method of example C46, in which the mesh structure includes a plurality of serpentine bridges.

Example C51 includes the method of example C46, further including incorporating the inverted F antenna into an adhesive.

Example C52 includes the method of example C51, in which the adhesive includes a medical grade adhesive configured for positioning on human skin.

Example C53 includes the method of example C51, in which the adhesive is configured for adhering to a nonorganic surface.

Example C54 includes the method of example C46, in which the weakly-adhesive material is configured to releasably adhere to the heat and moisture resistant material.

Example C55 includes the method of example C54, further including releasing the thin metal film from the weakly-adhesive material.

Example C56 includes the method of example C46, in which the heat and moisture resistant material includes a polyimide film.

Example C57 includes the method of example C46, in which the weakly-adhesive material includes polydimethylsiloxane (PDMS).

Example C58 includes the method of example C46, in which depositing the thin metal film includes metal sputter deposition.

Example C59 includes the method of example C46, in which patterning the thin metal film includes wet etching.

Example C60 includes the method of example C46, in which providing the flexible and stretchable inverted F antenna includes providing an inverted F antenna including a ground plane including a plurality of sensors.

Example C61 includes the method of example C60, in which the plurality of sensors includes at least one of a humidity sensor, a pressure sensor, a temperature sensor, a motion sensor and a location sensor.

Example C62 includes the method of example C60, in which the plurality of sensors includes at least one of electrocardiography (ECG), electromyography (EMG), electrogastrography (EGG), and electroencephalography (EEG) measurements.

Example C63 includes the method of example C46, in which providing the flexible and stretchable inverted F antenna includes providing an antenna configured to transmit at a frequency of 2.4 GHz.

Example C64 includes the method of example C46, in which providing the flexible and stretchable inverted F antenna includes providing an antenna configured to stretch up to 150% of an initial length.

Example C65 includes the method of example C46, in which providing the flexible and stretchable inverted F antenna includes providing an antenna configured to be at least as stretchable as human skin.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A flexible and stretchable antenna device, comprising:
    an adhesive substrate having flexible and stretchable material properties and structured to adhere to a surface of an object; and
    an antenna coupled to the adhesive substrate, the antenna including a radiating antenna part and an antenna ground part that are configured to operate to transmit or receive a wireless communication signal, wherein at least a part of the antenna ground part is structured as a mesh structure allowing the antenna to transmit or receive the wireless communication signal at a predetermined operating frequency while being stretched,
    wherein the mesh structure of the antenna ground part includes electrodes each of which is configured to: collect signals from the object and, at the same time, operate as a part of the antenna device for simultaneous collection of the signals and transmission of the collected signals in the wireless communication signal at the predetermined operating frequency.

2. The antenna device of claim 1, wherein the antenna includes a structural layout configured as an inverted F antenna (IFA).

3. The antenna device of claim 2, wherein the IFA is structured to include the radiating antenna part having a terminal end that aligns with one end side of the antenna ground part, and the antenna ground part having a substantially rectangular geometry.

4. The antenna device of claim 2, wherein the IFA includes an antenna feed part that extends from proximate the radiating antenna part into a void region of the antenna ground part without making contact with the antenna ground part to interface with an electrical circuit or electronic device on the adhesive substrate.

5. The antenna device of claim 2, wherein the IFA includes a mark on one or both of the antenna and the adhesive substrate indicating a line to cut the antenna device to remove a portion of the antenna device and thereby modify the antenna device such that a user can define an operating frequency of the modified antenna device.

6. The antenna device of claim 5, wherein the mark is oriented on the antenna device based on a second predetermined operating frequency different than the first predetermined operating frequency associated with the object.

7. The antenna device of claim 2, wherein the IFA is electrically connected to one or more sensors to measure at least one of electromyography (EMG) signals, electrocardiography (EKG), electroencephalography (EEG) signals, electrogastrography (EGG), electrooculography (EOG), electrochemical signals, temperature measurements, humidity measurements, pressure measurements, motion, or location.

8. The antenna device of claim 2, wherein the antenna ground part of the IFA includes an array of electrodes formed by elements of the mesh structure.

9. The antenna device of claim 1, wherein the electrodes in the mesh structure are configured to collect physiological signals from a living subject.

10. The antenna device of claim 9, wherein the collected physiological signals include one or more of electromyography (EMG) signals, electrocardiography (EKG), electroencephalography (EEG) signals, electrogastrography (EGG), electrooculography (EOG), electrochemical signals, temperature measurements, or humidity measurements.

11. The antenna device of claim 1, wherein the electrodes in the mesh structure are configured to collect data pertaining to use of a medical treatment container.

12. The antenna device of claim 11, wherein the collected data includes a detection of an external contact with or motion of the surface to which the antenna device is adhered.

13. The antenna device of claim 1, wherein the object is a living subject, and the surface to adhere the flexible and stretchable antenna device is skin of the living subject.

14. The antenna device of claim 1, wherein the object is a non-animate object.

15. The antenna device of claim 14, wherein the surface of the non-animate object to adhere the flexible and stretchable antenna device includes one or more of a plastic or a glass.

16. The antenna device of claim 1, wherein the adhesive substrate includes a medical-grade adhesive material.

17. The antenna device of claim 16, wherein the medical grade adhesive material includes tegaderm.

18. The antenna device of claim 1, wherein the adhesive substrate includes a heat and moisture resistant material.

19. The antenna device of claim 18, wherein the heat and moisture resistant material includes a polyamide film.

20. The antenna device of claim 1, wherein the antenna includes a metal film including at least one of gold or chromium.

21. The antenna device of claim 1, wherein the antenna device is configured to be stretchable of at least 50% in multiple directions.

22. The antenna device of claim 1, wherein the mesh structure includes an array of features interleaved with openings, the features having a size smaller than the wavelength associated with the wireless communication signal at the predetermined operating frequency.

23. The antenna device of claim 1, wherein the radiating antenna part includes the mesh structure.

* * * * *